US011813247B2

(12) United States Patent
Chase et al.

(10) Patent No.: US 11,813,247 B2
(45) Date of Patent: *Nov. 14, 2023

(54) NK-1 ANTAGONIST COMPOSITIONS AND METHODS FOR USE IN TREATING DEPRESSION

(71) Applicant: CHASE THERAPEUTICS CORPORATION, Washington, DC (US)

(72) Inventors: Thomas N. Chase, Washington, DC (US); Kathleen E. Clarence-Smith, Washington, DC (US)

(73) Assignee: CHASE THERAPEUTICS CORPORATION, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,016

(22) Filed: Feb. 14, 2022

(65) Prior Publication Data

US 2022/0168281 A1    Jun. 2, 2022

Related U.S. Application Data

(62) Division of application No. 16/612,819, filed as application No. PCT/US2018/039883 on Jun. 28, 2018, now Pat. No. 11,266,633.

(60) Provisional application No. 62/527,215, filed on Jun. 30, 2017.

(51) Int. Cl.
*A61K 31/428* (2006.01)
*A61K 31/438* (2006.01)
*A61K 31/5377* (2006.01)

(52) U.S. Cl.
CPC .......... *A61K 31/428* (2013.01); *A61K 31/438* (2013.01); *A61K 31/5377* (2013.01)

(58) Field of Classification Search
CPC .................................................. A61K 31/428
See application file for complete search history.

(56) References Cited

U.S. PATENT DOCUMENTS

| | | | |
|---|---|---|---|
| 6,191,153 B1 | 2/2001 | Hammer et al. | |
| 6,255,329 B1 | 7/2001 | Maj | |
| 6,271,230 B1 | 8/2001 | Baker et al. | |
| 6,620,438 B2 * | 9/2003 | Pairet ..................... | A61K 9/008 424/46 |
| 6,667,329 B1 | 12/2003 | Maj | |
| 8,877,768 B2 | 11/2014 | Chase et al. | |
| 11,160,809 B2 * | 11/2021 | Chase .................. | C07D 277/82 |
| 11,266,633 B2 * | 3/2022 | Chase ................. | A61K 31/5377 |
| 2007/0225279 A1 | 9/2007 | Rosenzweig-Lipson | |
| 2011/0071135 A1 | 3/2011 | Chase et al. | |
| 2014/0024644 A1 | 1/2014 | Hitchcock et al. | |
| 2015/0344474 A1 | 12/2015 | Davoren et al. | |
| 2016/0264597 A1 | 9/2016 | Chytil et al. | |
| 2017/0001987 A1 | 1/2017 | Xie et al. | |

FOREIGN PATENT DOCUMENTS

| | | |
|---|---|---|
| CN | 110730662 A | 1/2020 |
| JP | 8-504201 A | 5/1996 |
| JP | 2001-502311 A | 2/2001 |
| JP | 2001-504847 A | 4/2001 |
| JP | 2002-520273 A | 7/2002 |
| JP | 2005-513068 A | 5/2005 |
| JP | 2013-505235 A | 2/2013 |
| WO | 98/15277 A2 | 4/1998 |
| WO | 98/24438 A1 | 6/1998 |
| WO | 03/051840 A1 | 6/2003 |
| WO | 2005/084654 A2 | 9/2005 |
| WO | 2011/034568 A1 | 3/2011 |
| WO | 2016/106135 A1 | 6/2016 |
| WO | 2017/049158 A1 | 3/2017 |
| WO | 2018/183192 A | 10/2018 |
| WO | 2018/191160 A1 | 10/2018 |

OTHER PUBLICATIONS

International Search Report of PCT/US2018/039883 dated Sep. 11, 2018 [PCT/ISA/210].
Written Opinion of PCT/US2018/039883 dated Sep. 11, 2018 [PCT/ISA/237].
Communication, dated Jul. 2, 2021, issued by Patent Office of the People's Republic of China in counterpart application No. 2018800506607.
Barone et al., "Pramipexole for the treatment of depressive symptoms in patients with Parkinson's disease: a randomised, double-blind, placebo-controlled trial", Lancet Neurol, vol. 9, No. 6, pp. 573-580, Jun. 2010 (8 pages total).
Corrigan et al., "Comparison of Pramipexole, Fluoxetine, and Placebo in Patients With Major Depression", Depression and Anxiety, vol. 11, No. 2, pp. 58-65, 2000 (8 pages total).
Cusin et al., "A randomized, double-blind, placebo-controlled trial of pramipexole augmentation in treatment-resistant major depressive disorder", J. Clin Psychiatry, vol. 74, No. 7, pp. e636-e641, Jul. 2013 (6 pages total).
Dell'Osso et al., "Assessing efficacy/effectiveness and safety tolerability profiles of adjunctive pramipexole in bipolar depression: acute versus long-term data", International Clinical Psychopharmacology, vol. 28, No. 6, pp. 297-304, Nov. 2013 (8 pages total).
De Sousa et al., "Challenging Treatment-Resistant Major Depressive Disorder: A Roadmap for Improved Therapeutics", Current Neuropharmacology, vol. 13, pp. 616-635, 2015 (20 pages total).
Fawcett et al., "Clinical Experience With High-Dosage Pramipexole in Patients With Treatment-Resistant Depressive Episodes in Unipolar and Bipolar Depression", Am J Psychiatry, vol. 173, No. 2, pp. 107-111, Feb. 2016 (5 pages total).
Goldberg et al., "Preliminary Randomized, Double-Blind, Placebo-Controlled Trial of Pramipexole Added to Mood Stabilizers for Treatment-Resistant Bipolar Depression", Am J Psychiatry, vol. 161, No. 3, pp. 564-566, Mar. 2004 (3 pages total).

(Continued)

*Primary Examiner* — Golam M Shameem
(74) *Attorney, Agent, or Firm* — Sughrue Mion, PLLC

(57) ABSTRACT

The present invention describes the combination of a NK1-antagonist with pramipexole or a pharmaceutically acceptable salt or solvate thereof, useful for treating depressive disorders, including major depressive disorder.

6 Claims, No Drawings

(56) References Cited

OTHER PUBLICATIONS

Hori et al., "The Efficacy of Pramipexole, a Dopamine Receptor Agonist, as an Adjunctive Treatment in Treatment-Resistant Depression: An Open-Label Trial", The Scientific World Journal, vol. 2012, Article ID 372474, 2012 (9 pages total).
Kleeblatt et al., "Efficacy of off-label augmentation in unipolar depression: A systematic review of the evidence", European Neuropsychopharmacology, vol. 27, pp. 423-441, Mar. 2017 (9 pages total).
Pae, "Pramipexole augmentation in treatment-resistant major depressive disorder", Expert Review of Neurotherapeutics, vol. 14, No. 1, pp. 5-8, 2014 (5 pages total).
Piercey, "Pharmacology of pramipexole, a dopamine $D_3$-preferring agonist, useful in treating Parkinson's disease", Clinical Neuropharmacology, vo. 21, No. 3, pp. 141-151, 1998 (11 pages total).
Poon et al., "Pharmacological Approaches for Treatment-resistant Bipolar Disorder", Current Neuropharmacology, vol. 13, No. 5, pp. 592-604, 2015 (13 pages total).
Schneider et al., "Dopamine Autoreceptor Agonists: Resolution and Pharmacological Activity of 2,6-Diaminotetrahydrobenzothiazole and an Aminothiazole Analogue of Apomorphine", J. Med Chem., vol. 30, No. 3, pp. 494-498, Mar. 1987 (5 pages total).
Sienaert et al., "Evidence-based treatment strategies for treatment-resistant bipolar depression: a systematic review", Bipolar Disorders, vol. 15, No. 1, pp. 61-69, Feb. 2013 (9 pages total).
Tondo et al., "Options for pharmacological treatment of refractory bipolar depression", Curr Psychiatry Rep., vol. 16, No. 2, vol. 431, Feb. 2014 (7 pages total).
Willner et al., "Reversal of stress-induced anhedonia by the dopamine agonist, pramipexole", Psychopharmacolgy, vol. 115, pp. 454-462, 1994 (9 pages total).
Szegedi et al., "Pramipexole, a Dopamine Agonist, in Major Depression: Antidepressant Effects and Tolerability in an Open-Label Study with Multiple Doses", Clinical Neuropharmacology, vol. 20, Suppl. 1, pp. S36-S45, 1997 (11 pages total).
Bétry et al., "Role of 5-$HT_3$ Receptors in the Antidepressant Response", Pharmaceuticals, vol. 4, pp. 603-629, 2011 (27 pages total).
Smith et al., "5-HT3 receptor antagonists for the treatment of nausea/vomiting", Ann Palliat Med, vol. 1, No. 2, pp. 115-120, 2012 (6 pages total).
Communication (Rejection Decision) dated Mar. 22, 2022 issued by Patent Office of the People's Republic of China in related application No. 201880050660.7.
Communication (Official Notification) dated Oct. 25, 2021 issued by Eurasian Patent Office in related application No. 202090180.
Communication (Official Notification) dated Jun. 6, 2022 issued by Eurasian Patent Office in related application No. 202090180.
Communication (Extended European Search Report) dated Feb. 19, 2021 for related European Patent Application No. 18824955.1.
Communication (Examination Report) dated Oct. 29, 2021 for related European Patent Application No. 18 824 955.1.
Communication (Examination Report) dated Oct. 6, 2022 for related European Patent Application No. 18 824 955.1.
Communication (First Examination Report) dated Mar. 24, 2021 for related Indian Patent Application No. 202017003521.
Communication (Date of Hearing) dated Oct. 27, 2022 for related Indian Patent Application No. 202017003521.
Communication (Office Action) dated Jun. 12, 2022 for related Israeli Patent Application No. 271464.
Communication (Notice of Reasons for Rejection) dated Feb. 15, 2022 for related Japanese Patent Application No. 2019-572041.
Communication (Decision for Patent) dated Sep. 13, 2022 for related Japanese Patent Application No. 2019-572041.
Communication (Office Action) dated Sep. 24, 2021 for related Mexican Patent Application No. MX/a/2019/015150.
Communication (Office Action) dated Feb. 18, 2022 for related Mexican Patent Application No. MX/a/2019/015150.
Communication (Office Action with Search Report) dated Feb. 18, 2022 for related Taiwanese Patent Application No. 107122579.
Communication (Decision) dated Sep. 29, 2022 for related Taiwanese Patent Application No. 107122579.
Mark S Kramer et al, "Demonstration of the Efficacy and Safety of a Novel Substance P (NK1) Receptor Antagonist in Major Depression", Neuropsychopharmacology (2004) 29, 385-392.
Kramer M.S. et al., "Distinct mechanism for antidepressant activity by blockade of central substance P receptors", SCIENCE, Sep. 11, 1998, vol. 281, p. 1640-1645.

\* cited by examiner

NK-1 ANTAGONIST COMPOSITIONS AND METHODS FOR USE IN TREATING DEPRESSION

RELATED APPLICATIONS

This application is a divisional of U.S. application Ser. No. 16/612,819, filed Nov. 12, 2019, which is a National Stage of International Application No. PCT/US2018/039883, filed Jun. 28, 2018, which claims the benefit of U.S. Provisional Patent Application Ser. No. 62/527,215, filed on Jun. 30, 2017, the disclosures of which are incorporated herein by reference in their entirety.

FIELD OF THE INVENTION

The present invention pertains to the field of the treatment of depression.

OBJECT OF THE INVENTION

The present invention includes pharmaceutical combinations comprising the (S)-6-propylamino-4,5,6,7-tetrahydro-1,3-benzothiazole-2-amine or a pharmaceutically acceptable salt or solvate thereof and an antagonist of the neurokinin receptor subtype-1 ("$NK_1$-antagonist"), including fixed-dose combinations, and their use for the treatment of major depressive disorders.

The present invention also includes methods for treating depressive disorders by administration of an antagonist of the neurokinin receptor subtype-1 (herein below referred to as "NK1-antagonist") in combination with a pramipexole daily dose that is from up to 10 times, from up to 4.7 times, or from 1.1 times to 10 times the maximum pramipexole daily dose recommended for the relief of the motor symptoms of Parkinson's disease. The invention also includes use of a NK1-antagonist for the treatment of depressive disorders in combination with a pramipexole daily dose that is from up to 10 times, from up to 4.7 times, or from 1.1 times to 10 times higher than the maximum pramipexole daily dose recommended for the relief of the motor symptoms of Parkinson's disease. The invention also includes a pharmaceutical composition comprising, as an active ingredient, a high dose of (S)-6-propylamino-4,5,6,7-tetrahydro-1,3-benzothiazole-2-amine or pharmaceutically acceptable salt or solvate thereof, in combination with a NK1-antagonist.

DEFINITIONS

"CGI": Clinical Global Impression.
"CNS": Central Nervous System.
"IR": Immediate Release of the active ingredient from a composition.
"ER": Extended Release of the active ingredient from a composition.
"GI": Gastro-Intestinal.
"AE(s)": Adverse Effect(s).
"DSM-5": Diagnostic and Statistical Manual of Mental Disorders, 5$^{th}$ edition.
"HAMD": Hamilton Depression Rating Scale.
"MADRS": Montgomery and Asberg Depression Rating Scale.
"MDD": Major Depressive Disorder.
"MAOIs": Monoamine oxidase inhibitors.
"NIMH": National Institute of Mental Health.
"PD": Parkinson's Disease.
"Persistent depressive disorder": also called dysthymia.
"PMDD": Premenstrual Dysphoric Disorder.
"NK1-antagonist": an antagonist of the neurokinine receptor subtype-1, in the literature also referred to as NK1 receptor antagonist or NK1 receptor inhibitor.
"Effective daily dose of NK1-antagonist": as used herein, refers to a daily dose of said NK1-antagonist of from 1 µg to 600 mg.
"Pramipexole": the (S)-6-propylamino-4,5,6,7-tetrahydro-1,3-benzothiazole-2-amine, as active principle including the free base and its pharmaceutically acceptable salts and solvates, unless otherwise specified.
"Effective daily dose of pramipexole" or "therapeutically effective dose of pramipexole": a daily pramipexole dose equivalent to at least a pramipexole dihydrochloride monohydrate approved daily dose for the treatment of PD, this effective daily dose including low daily doses used during the titration period.
"Effective dose/unit form" or "effective dose per unit form", in reference to pramipexole: a pramipexole amount per unit form equivalent to at least a pramipexole dihydrochloride monohydrate amount per unit form approved for the treatment of PD, this amount including low amounts per unit form used during the titration period.
"Salts or solvates thereof" or "salts and solvates thereof", with reference to any NK1-antagonist or to pramipexole: this expression indicates that any salt of said pramipexole or said NK1-antagonist may be solvated with a solvent, normally water.
"SSRIs": Selective serotonin reuptake inhibitors.
"NDRIs": Norepinephrine-dopamine reuptake inhibitors.
"TCAs": Tricyclic antidepressants.
"TTS": Transdermal Therapeutic System.
"Depressive disorders": include, but are not limited to, major depressive disorder (MDD), persistent depressive disorder (dysthymia), Bipolar depression, seasonal affective disorder (SAD), psychotic depression, premenstrual dysphoric disorder (PDD), peripartum (postpartum) depression, situational depression, and atypical depression. The common feature of these depressive disorders is the presence of sad, empty, or irritable mood, accompanied by somatic and cognitive changes that significantly affect the individual's capacity to function. The difference among these disorders are issues of duration, timing or presumed etiology. See Depressive Disorders, Diagnostic and Statistical Manual of Mental Disorders, Fifth Edition, dsm.psychiatryonline.org/doi/10.1176/appi.books.9780890425596.dsm04.
"Maximum tolerated dose," "maximal tolerated dose" or "MTD" refers to, and is defined as the highest dose of a drug or treatment that does not cause unacceptable side effects. For instance, the maximum tolerated dose is determined in clinical trials by testing increasing doses on different groups of people until the highest dose with acceptable side effects is found. The dose of the pramipexole may be higher than the maximum tolerated dose of pramipexole for the treatment of depression when administered alone. In particular, from 1.1 to 10 times higher than the maximal tolerated dose of pramipexole for the treatment of depression when administered alone, which includes, but is not limited to a dose from 1.5 to 10 times higher than the maximal tolerated dose of pramipexole for the treatment of depression when administered alone, a dose from 2.5 to 10 times higher than the maximal tolerated dose of pramipexole for the treatment of depression when administered alone, a dose from 3 to 10 times higher than the maximal tolerated dose of pramipexole for the treatment of depression when administered alone, a dose from 4 to 10 times higher than the maximal tolerated dose of pramipexole for the treatment of depression when administered alone, and a dose from 6 to 10 times higher than the maximal tolerated dose of pramipexole for the treatment of depression when administered alone.

BACKGROUND OF THE INVENTION

Major depressive disorder (MDD), also referred to as depression or clinical depression, is a common but serious mood disorder associated with a significant burden, affecting around 16% of the population in the US in their lifetime (reviewed in de Souza et al, 2015). Depression is one of the most common mental disorders in the U.S. Current research suggests that depression is caused by a combination of genetic, biological, environmental, and psychological factors.

The estimated costs of MDD are around 83 billion US Dollars annually, due to many psychosocial factors including loss of workdays (reviewed in de Souza et al, 2015). Estimates are that on average a depressed person loses 27.2 workdays per year (reviewed in de Souza et al, 2015). A significant part of the burden corresponds to unsuccessful treatments. Remission of depressive symptoms is achieved in only one-third of the MDD patients after the first antidepressant trial (reviewed in de Souza et al, 2015), and unsuccessful treatments contribute substantially to the observed suffering and social costs of MDD.

Signs and symptoms of depression typically include the following: persistent sad, anxious, or "empty" mood; feelings of hopelessness, or pessimism; irritability; feelings of guilt, worthlessness, or helplessness; loss of interest or pleasure in hobbies and activities; decreased energy or fatigue; moving or talking more slowly; feeling restless or having trouble sitting still; difficulty concentrating, remembering, or making decisions; difficulty sleeping, early-morning awakening, or oversleeping; appetite and/or weight changes; thoughts of death or suicide, or suicide attempts; aches or pains, headaches, cramps, or digestive problems without a clear physical cause and/or that do not ease even with treatment (NIMH, Health and Education, Mental Health Information as posted on the NIMH Web Site). Not everyone who is depressed experiences every symptom. Some people experience only a few symptoms while others may experience many. For a diagnosis of depression, signs and symptoms have to be present most of the day, nearly every day, for at least two weeks (DSM-5)

Depression can happen at any age (NIMH, Health and Education, Mental Health Information as posted on the NIMH Web Site), but often begins in adulthood. Depression is now recognized as occurring in children and adolescents, although it sometimes presents with more prominent irritability than low mood. Depression, especially in midlife or older adults, can co-occur with other serious medical illnesses, such as diabetes, cancer, heart disease, and Parkinson's disease. Risk factors include: personal or family history of depression; major life changes, trauma, or stress; certain physical illnesses and medications.

Some forms of depression are slightly different, or develop under unique circumstances (NIMH, Health and Education, Mental Health Information as posted on the NIMH Web Site), such as:

Persistent depressive disorder (also called dysthymia) with early or late onset and with or without atypical features, is a depressed mood that lasts for at least two years. A person diagnosed with persistent depressive disorder may have episodes of major depression along with periods of less severe symptoms, but symptoms must last for two years to be considered persistent depressive disorder.

Perinatal depression is much more serious than the "baby blues" (relatively mild depressive and anxiety symptoms that typically clear within two weeks after delivery) that many women experience after giving birth. Women with perinatal depression experience full-blown major depression during pregnancy or after delivery (postpartum depression). The feelings of extreme sadness, anxiety, and exhaustion that accompany perinatal depression may make it difficult for these new mothers to complete daily care activities for themselves and/or for their babies.

Psychotic depression occurs when a person has severe depression plus some form of psychosis, such as having disturbing false fixed beliefs (delusions) or hearing or seeing upsetting things that others cannot hear or see (hallucinations). The psychotic symptoms typically have a depressive "theme," such as delusions of guilt, poverty, or illness.

Seasonal affective disorder is characterized by the onset of depression during the winter months, when there is less natural sunlight. This depression generally lifts during spring and summer. Winter depression, typically accompanied by social withdrawal, increased sleep, and weight gain, predictably returns every year in seasonal affective disorder.

Mood dysregulation disorder (diagnosed in children and adolescents; DSM-5).

Premenstrual Dysphoric Disorder (PMDD; DSM-5).

Bipolar Disorder is different from depression, but it is included in this list because patients with bipolar disorder experience episodes of extremely low moods that meet the criteria for major depression (called "bipolar depression"). Bipolar disorder is a persistent, episodic and debilitating condition with an estimated lifetime prevalence of over 2.0%, including both types I (with mania) and II (with hypomania) (reviewed in Poon et al, 2015). Bipolar disorder is associated with recurring episodes of mania, hypomania, mixed manicdepressive states, or psychosis, as well as prominent major depression and dysthymia, as well as prevalent anxiety symptoms—all leading to high risks of potentially severe functional impairment, substance abuse, and high rates of suicide, accidents, and increased mortality from co-occurring medical illnesses—all despite use of available pharmacological and psychosocial treatments (Poon et al, 2015). The depressive components of the disorder have been especially difficult to treat successfully and they account for three-quarters of the several weeks of follow-up with treatment that include clinically significant residual morbidity (reviewed in Poon et al, 2015).

Other mood disorders encompassed within the term "depression" include Alzheimer's disease with depressed mood, depressed mood in Parkinson's disease, Lewy body disease, and other dementias, post-stroke depression, schizoaffective disorders, adjustment disorder with depressed mood, and drug- and alcohol-induced depressed mood.

Depression is usually initially treated with medications and psychotherapy. If the treatments do not reduce symptoms, electroconvulsive therapy and other brain stimulation therapies may help. Medications include the following (Mayo Clinic):

Selective serotonin reuptake inhibitors (SSRIs) such as fluoxetine (Prozac), paroxetine (Paxil, Pexeva), sertraline (Zoloft), citalopram (Celexa) and escitalopram (Lexapro).

Serotonin-norepinephrine reuptake inhibitors (SNRIs) such as duloxetine (Cymbalta), venlafaxine (Effexor XR), desvenlafaxine (Pristiq, Khedezla) and levomilnacipran (Fetzima).

Norepinephrine-dopamine reuptake inhibitors (NDRIs). Bupropion (Wellbutrin, Aplenzin, Forfivo XL) falls into this category.

Atypical antidepressants such as trazodone and mirtazapine (Remeron), vortioxetine (Brintellix) and vilazodone (Viibryd).

Tricyclic antidepressants (TCAs) such as imipramine (Tofranil), nortriptyline (Pamelor), amitriptyline, doxepin, trimipramine (Surmontil), desipramine (Norpramin) and protriptyline (Vivactil)—can be very effective, but tend to cause more-severe side effects than newer antidepressants. Tricyclics are therefore usually considered as second line therapy.

Monoamine oxidase inhibitors (MAOIs), such as tranylcypromine (Parnate), phenelzine (Nardil) and isocarboxazid (Marplan), may be prescribed, typically when other medications haven't worked. However, MAOIs are usually not first line antidepressant therapy, because they can have serious interactions with certain foods and some medications including birth control pills, decongestants and certain herbal supplements. Selegiline TTS (Emsam), a newer MAOI, may cause fewer side effects than other MAOIs.

One disadvantage of all of the above antidepressant medications is that they typically take 2 to 4 weeks to start having an antidepressant effect.

(S)-6-propylamino-4,5,6,7-tetrahydro-1,3-benzothiazole-2-amine (pramipexole) is a synthetic aminothiazole derivative, described in U.S. Pat. No. 4,886,812, the content of which is incorporated herein by reference. It is a dopamine autoreceptor agonist (Schneider and Mierau 1987) that is approved for the treatment of the symptoms of Parkinson's disease (PD), in doses ranging from 0.375 mg/day to 4.5 mg/day, given in 3 equally divided doses (Mirapex® Prescribing Information May 2018) or in a single dose once a day (Mirapex ER® Prescribing Information, July 2016). Pramipexole is supplied in tablets for immediate release containing 0.125 mg, 0.25 mg, 0.5 mg, 1 mg and 1.5 mg of pramipexole dihydrochloride monohydrate; and in tablets for extended release containing 0.375 mg, 0.75 mg, 1.5 mg, 3 mg and 4.5 mg of pramipexole dihydrochloride monohydrate. It is structurally distinct from the ergot-derived drugs (e.g., bromocriptine and pergolide). Pramipexole is a dopamine D2 receptor agonist that is also pharmacologically unique in that it is a full agonist and has receptor selectivity for the dopamine D3 receptor subtype of the D2 subfamily of receptors. These properties may confer advantages in terms of both efficacy (full agonist with potential for greater therapeutic effects) and safety (receptor selectivity may reduce unwanted side effects) compared to currently available dopamine agonists (Piercey, 1998).

Literature reports that pramipexole was also found to be effective in the treatment of depressive symptoms in patients with PD, albeit with a small effect size. A 12-week, double-blind, placebo controlled trial in 296 PD patients was conducted with pramipexole (0.125 to 1.0 mg given three times per day). The primary endpoint was the Beck Depression Inventory scale (BDI). Results showed that BDI scores decreased by an adjusted 5.9 (SE 0.5) in the pramipexole group, and 4.0 (SE 0.5) in the placebo group. The difference between the 2 treatment groups was significant (p=0.01; Barone et al, 2010), although the magnitude of the effect size was small. In addition, other small, often open-label studies in which pramipexole was added on to antidepressant treatment (augmentation) also showed modest but significant efficacy in favor of pramipexole in non-PD patients with major depressive disorder (MDD; Cusin et al, 2013; Goldberg et al, 2004), including non-PD patients with treatment resistant depression (Hori and Kunigi, 2012; Pae, et al, 2013; Fawcett et al, 2016), or patients with depression associated with bipolar disorder (reviewed in Sienaert et al, 2013; Dell'Osso and Ketter, 2013; Tondo et al, 2014). However, Kleebatt et al (2017) in their review judged that clear proof of antidepressant efficacy had not been obtained for pramipexole, and attributed this to low levels of evidence, small sample sizes or discordant results. In all these reports, the dose of pramipexole remained within the range approved for the treatment of the motor symptoms of PD, even when the title of the publication mentions "high doses" of pramipexole (Fawcett et al, 2016). Since in most of these studies, efficacy appeared to be modest, higher doses of pramipexole were tested in a randomized, prospective, double-blind, placebo-controlled, fixed-dose study (Corrigan et al, 2000). A total of 174 eligible patients with a DSM-III-R diagnosis of major depression (single or recurrent episode, with or without melancholia and without psychotic features) were assigned to one of five treatment groups: placebo group, fluoxetine group (20 mg/day), or one of three pramipexole groups (0.375 mg/day; 1 mg/day; 5 mg/day). Patients received a 1-week placebo run-in, 8 weeks of treatment, and a 1-week post-study follow-up assessment (week 9). Efficacy was measured primarily by the change from baseline in the HAM-D (17-item version) total score, MADRS total score, and the CGI-Severity of Illness (SI) score. Results showed that the majority of patients in each treatment group completed the study (66-86%), with the exception of the pramipexole 5.0 mg group (42.4%). In the pramipexole 5.0 mg group, 57.6% of patients discontinued treatment prematurely, mainly because of adverse events (AEs), 76% of patients reported nausea, and 39% reported vomiting. At endpoint (week 8), the pramipexole 1.0 mg group and the fluoxetine group showed significantly better improvement over baseline than the placebo group on the HAMD (p=0.0076) and on the MADRS. The pramipexole 5.0 mg group had the best improvement at week 8 (−15.00), but p values were not available for this test against placebo because of the high drop-out rate.

Taken together, the results reported by Corrigan et al (2000) suggest that higher doses of pramipexole could be more effective, but doses higher than the approved doses cannot be used because of a high incidence of dose-limiting adverse events (AEs), notably nausea and vomiting but also non-G.I. adverse effects such as diaphoresis, light headedness and headache. Also, animal studies support the suggestion that high doses of pramipexole should be more effective for the treatment of depression. For example, high doses of pramipexole proved to be active in diverse tests of animal behavior simulating symptoms of depression, including Willner's Anhedonia Test (Willner et al., 1994), Fixed Interval Test, Forced Swimming Test, and REM Sleep Inhibition Test.

Due to the pramipexole AEs, however, the problem of providing safe, chronic, effective treatment of a patient suffering from depression with pramipexole has remained unsolved.

SUMMARY OF THE INVENTION

The present invention relates to increasing the therapeutic window for pramipexole, for the treatment of depressive disorders, including MDD, to safely enable its full antidepressant efficacy. In particular, the present invention relates to a combination of a NK1-antagonist with pramipexole, to increase the therapeutic window of said pramipexole.

It has been found that a NK1-antagonist, by reducing or even abrogating the side effects of high doses of pramipexole, enables the full antidepressant potential of pramipexole.

Thus, the safe administration of pramipexole doses that are higher, and even much higher, than the maximum daily dose recommended for the relief of the symptoms of Parkinson's disease (such as motor symptoms), provides significant improvement to patients suffering from depressive disorders.

Alternatively, the safe administration of pramipexole doses that are higher, and even much higher than the maximum tolerated dose for the relief of symptoms of Parkinson's disease (such as motor symptoms), provides significant improvement to patients suffering from depressive disorders.

More particularly, it has been found that, in the case of pramipexole dihydrochloride monohydrate, its combination with said NK1-antagonist allows the administration of a therapeutic effective dose of said pramipexole dihydrochloride monohydrate that will significantly exceed the maximum recommended dose (4.5 mg/day) of pramipexole dihydrochloride monohydrate for the treatment of the symptoms of PD, thus increasing its efficacy in the treatment of a patient suffering from a depressive disorder, including MDD.

More particularly, it has been found that the combination of pramipexole or a pharmaceutically acceptable salt or solvate thereof with a NK1-antagonist allows the administration of a therapeutic effective dose that may be equivalent to from up to 10 times, from up to 4.7 times, or from 1.1 times to 10 times higher than the aforementioned maximum dose of pramipexole dihydrochloride monohydrate recommended for the treatment of the symptoms of PD.

The combination of a NK1-antagonist with pramipexole or a pharmaceutically acceptable salt or solvate thereof acts by enabling the full antidepressant efficacy of pramipexole, due to the high pramipexole doses that may be used in combination with said NK1-antagonist.

It has also been found that, in patients suffering from a depressive disorder, daily doses of pramipexole (in pramipexole dihydrochloride monohydrate) ranging from more than 4.5 mg to 45 mg/day, up to from 15 mg to 45 mg/day, in combination with a NK1-antagonist normally indicated for the prevention of postoperative nausea and vomiting or of the chemotherapy-induced nausea and vomiting, offer significant efficacy and a fast onset of action.

More particularly, it been found that, in the treatment of patients suffering from a depressive disorder, the use of a NK1-antagonist in combination with daily doses of pramipexole or pharmaceutically acceptable salt or solvate thereof that are equivalent to from more than 4.5 mg to 21 mg/day and even from more than 6 mg to 21 mg or from 15 mg to 21 mg of pramipexole dihydrochloride monohydrate, also offer significant efficacy and a fast onset of action.

It has also been found that, by using said NK1 receptor antagonist, also referred to as NK1 receptor inhibitor or simply NK1-antagonist, in combination with pramipexole or a pharmaceutically acceptable salt or solvate thereof, it is possible to treat a patient suffering from depression by maintaining an effective pramipexole or pharmaceutically acceptable salt or solvate thereof daily dose with minimal adverse effect.

Thus, the present invention provides a pharmaceutical combination comprising
(a) a NK1-antagonist; and
(b) pramipexole or a pharmaceutically acceptable salt or solvate thereof.

In particular, the present invention provides a pharmaceutical combination comprising
(a) a NK1-antagonist; and
(b) pramipexole or a pharmaceutically acceptable salt or solvate thereof, at a daily dose (in pramipexole dihydrochloride monohydrate) that is higher than the maximum dose of pramipexole dihydrochloride monohydrate recommended for the relief of the motor symptoms of PD,
for use for the treatment of depressive disorders, including MDD.

Said pramipexole daily dose in said combination is from up to 10 times, from up to 4.7 times, or from 1.1 times to 10 times higher than the maximum dose of pramipexole dihydrochloride monohydrate recommended for the relief of the motor symptoms of PD.

The present invention further provides the use of a NK1-antagonist for enabling the full antidepressant efficacy of pramipexole in the treatment of MDD.

Moreover, the invention provides a method for treating a patient suffering from a depressive disorder, which comprises treating said patient with a NK1-antagonist, in combination with pramipexole or a pharmaceutically acceptable salt or solvate thereof.

Moreover, the invention provides a method for treating a patient suffering from a depressive disorder, which comprises treating said patient with a NK1-antagonist, in combination with pramipexole or a pharmaceutically acceptable salt or solvate thereof at a daily dose (in pramipexole dihydrochloride monohydrate) from up to 10 times, from up to 4.7 times, or from 1.1 times to 10 times higher than the maximum daily dose recommended for the relief of the symptoms of Parkinson's disease such as motor symptoms (4.5 mg/day).

The daily dose of the NK1-antagonist is from 1 µg to 600 mg and the pramipexole daily dose (in pramipexole dihydrochloride monohydrate), depending on the degree of gravity of the illness and the age and condition of the patient and including low doses for use during the titration period, will range from 0.375 mg to 45 mg, normally from 0.375 mg to 21 mg. For treating depression, said daily dose preferably is from more than 4.5 mg to 45 mg, from more than 6 mg to 45 mg, from 10 mg to 45 mg, from 13 mg to 45 mg, or from 15 mg to 45 mg, normally from more than 4.5 mg to 21 mg, in particular from more than 6 mg to 21 mg, from 10 mg to 21 mg, from 13 mg to 21 mg or from 15 mg to 21 mg.

According to an embodiment, for said use or said method, said NK1-antagonist, in an amount per unit form of from 1 µg to 600 mg or from 1 mg to 600 mg, and said pramipexole or pharmaceutically acceptable salt or solvate thereof, in an amount equivalent to from 0.125 mg to 45 mg, from more than 4.5 mg to 21 mg or from more than 6 mg to 21 mg, are each formulated in a pharmaceutical composition in admixture with a pharmaceutical carrier or vehicle and separately administered, concurrently or sequentially, to a patient in need of treatment with said combination, and in particular to a patient suffering from a depressive disorder, including MDD.

According to another embodiment, said NK1-antagonist and said pramipexole or pharmaceutically acceptable salt or solvate thereof are mixed together and formulated in a pharmaceutical composition (fixed-dose combination), in admixture with a pharmaceutical carrier, to be administered to a patient in need of said treatment.

According to this embodiment, said NK1-antagonist, in an amount of from 1 μg to 600 mg or from 1 mg to 600 mg, and said pramipexole or pharmaceutically acceptable salt or solvate thereof, in an amount equivalent to from 0.125 mg to 45 mg, preferably from more than 4.5 mg to 45 mg, from more than 6 mg to 45 mg, from 10 mg to 45 mg, from 13 mg to 45 mg, from 15 mg to 45 mg, from more than 4.5 mg to 21 mg or from more than 6 mg to 21 mg, from 10 mg to 21 mg, from 13 mg to 21 mg, from 15 mg to 21 mg of pramipexole dihydrochloride monohydrate, are mixed together and formulated in a pharmaceutical composition (fixed-dose combination), in admixture with a pharmaceutical carrier or vehicle, to be administered to a patient in need of said treatment.

According to the invention, said NK1-antagonist may also be formulated in a pharmaceutical composition comprising said NK1-antagonist in an amount per unit form of from 1 μg to 600 mg or from 1 mg to 600 mg, in admixture with a pharmaceutical carrier or vehicle, for use for preventing or curing the adverse effects of pramipexole daily doses that for some patients may be higher, and even much higher, than the maximum dose (4.5 mg/day) presently recommended for the relief of the motor symptoms of Parkinson's disease.

For its use for the treatment of a depressive disorder, including MDD, in combination with a NK1-antagonist, pramipexole is formulated in a pharmaceutical composition in dosage unit form comprising said pramipexole in an amount per IR- or ER-form (including low doses to be used during the titration period) equivalent to from 0.125 mg to 45 mg, advantageously from more than 4.5 mg to 45 mg, from more than 6 mg to 45 mg, from 10 mg to 45 mg, from 13 mg to 45 mg, or from 15 mg to 45 mg of pramipexole dihydrochloride monohydrate.

In particular, for said use in combination with a NK1-antagonist, pramipexole is formulated in a pharmaceutical composition in dosage unit form comprising said pramipexole an amount per IR-form (including low doses to be used during the titration period) equivalent to from 0.125 mg to 22.5 mg, advantageously from 1.5 mg to 22.5 mg, from more than 3 mg to 22.5 mg, from 5 mg to 22.5 mg, from 6.5 mg to 22.5 mg, or from 7.5 mg to 22.5 mg of pramipexole dihydrochloride monohydrate.

For said use in combination with a NK1-antagonist, pramipexole, is formulated in a pharmaceutical composition in dosage unit form comprising said pramipexole an amount per ER-form (including low doses to be used during the titration period) equivalent to from 0.375 mg to 45 mg, from more than 4.5 mg to 45 mg, from 5 mg to 45 mg, from more than 6 mg to 45 mg, from 10 mg to 45 mg from 13 mg to 45 mg, or from 15 mg to 45 mg of pramipexole dihydrochloride monohydrate.

According to an embodiment, the dose of pramipexole or pharmaceutically acceptable salt or solvate thereof, in pramipexole dihydrochloride monohydrate, per IR- or ER- unit form, will range from 0.125 mg to 21 mg, advantageously from 1.6 mg 21 mg, from 1.8 mg to 21 mg, from 2.4 mg to 21 mg, from 3 mg to 21 mg, more advantageously from more than 4.5 mg to 21 mg, preferably from more than 6 mg to 21 mg, from 10 mg to 21 mg, from 13 mg to 21 mg, or from 15 mg to 21 mg.

Preferably, according to this embodiment, the dose per unit form of pramipexole or pharmaceutically acceptable salt or solvate thereof in an ER formulation, including slow-release compositions and transdermal therapeutic systems such as transdermal patches, for the treatment of a depressive disorder, including MDD, will range from an amount that is equivalent to from more than 4.5 mg to 21 mg, in particular from 4.8 mg to 21 mg or from more than 6 mg to 21 mg of pramipexole dihydrochloride monohydrate, depending on the tolerability (in combination with said NK1-antagonist).

In the aforementioned combinations with pramipexole, at the above doses/unit form,
if the NK1-antagonist is aprepitant, the dose/unit form will range from 10 mg to 250 mg;
if the NK1-antagonist is rolapitant, the dose/unit form will range from 30 mg to 270 mg.

DETAILED DESCRIPTION

The present invention concerns a NK1-antagonist Component (a), as an adverse events inhibitor, in combination with pramipexole or a pharmaceutically acceptable salt or solvate thereof Component (b) at a daily dose equivalent to from up to 10 times, up to 4.7 times, or from 1.1 times to 10 times higher than the maximal pramipexole dihydrochloride monohydrate dose approved for the treatment of motor symptom of Parkinson's disease. Said combination, including fixed-dose combinations, is useful for the treatment of depressive disorders, including MDD. Said combination, including fixed-dose combinations, is also for use for the treatment of depressive disorders, including MDD.

The present invention also concerns a NK1-antagonist Component (a), as an adverse events inhibitor, in combination with pramipexole or a pharmaceutically acceptable salt or solvate thereof Component (b) at a daily dose equivalent to from 1.1 to 10 times higher than the maximal tolerated dose of pramipexole for the treatment of depression when administered alone. Such a daily dose includes, but is not limited to a dose from 1.1 to 10 times higher than the maximal tolerated dose of pramipexole for the treatment of depression when administered alone, a dose from 1.5 to 10 times higher than the maximal tolerated dose of pramipexole for the treatment of depression when administered alone, a dose from 2.5 to 10 times higher than the maximal tolerated dose of pramipexole for the treatment of depression when administered alone, a dose from 3 to 10 times higher than the maximal tolerated dose of pramipexole for the treatment of depression when administered alone, a dose from 4 to 10 times higher than the maximal tolerated dose of pramipexole for the treatment of depression when administered alone, and a dose from 6 to 10 times higher than the maximal tolerated dose of pramipexole for the treatment of depression when administered alone.

In particular, the invention concerns, according to its aspects,
a method for treating depressive disorders, including MDD by administration of a NK1-antagonist to a patient in combination with an effective pramipexole or pharmaceutically acceptable salt thereof daily dose;
a NK1-antagonist Component (a), for use for the treatment of depressive disorders, including MDD, in a patient, in combination with, as Component (b), a pramipexole or pharmaceutically acceptable salt or solvate thereof daily dose;
the use of a NK1-antagonist for the preparation of a medicament for the treatment of depressive disorders, including MDD, in a patient, in combination (including fixed-dose combination) with an effective daily dose of pramipexole or a pharmaceutically acceptable salt thereof;

the use of a NK1-antagonist for the preparation of a medicament for the treatment of a depressive disorder, including MDD, said medicament consisting of a pharmaceutical composition in dosage unit form comprising, as an active ingredient, said NK1-antagonist and, as another active ingredient, pramipexole or a pharmaceutically acceptable salt thereof; and a method (or use) of a NK1-antagonist as an inhibitor of the adverse effects of pramipexole in the treatment of a depressive disorder, including MDD.

The present invention also relates to a fixed-dose combination (a/b) comprising said NK1-antagonist Component (a) and said pramipexole or pharmaceutically acceptable salt or solvate thereof Component (b) in a pharmaceutical composition in dosage unit form in admixture with a pharmaceutically acceptable carrier or vehicle. This fixed-dose combination is useful and is for use for the treatment of depressive disorders, including MDD, in a patient.

The NK1-Antagonist Component (a)

Any of the NK1-antagonists disclosed in the literature is an useful adverse effect inhibitor of pramipexole and may be safely used, as Component (a), in combination with a dose of pramipexole or pharmaceutically acceptable salt or solvate thereof Component (b) that is equivalent to from up to 10 times, from up to 4.7 times, or from 1.1 times to 10 times higher than the maximum pramipexole dihydrochloride monohydrate daily dose recommended for the relief of the motor symptoms of PD.

Any of the NK1-antagonists disclosed in the literature is an useful adverse effect inhibitor of pramipexole and may be safely used, as Component (a), in combination with a dose of pramipexole or pharmaceutically acceptable salt or solvate thereof Component (b) that is equivalent to from 1.1 to 10 times higher than the maximal tolerated dose of pramipexole for the treatment of depression when administered alone. Such a dose includes, but is not limited to a dose from 1.1 to 10 times higher than the maximal tolerated dose of pramipexole for the treatment of depression when administered alone, a dose from 1.5 to 10 times higher than the maximal tolerated dose of pramipexole for the treatment of depression when administered alone, a dose from 2.5 to 10 times higher than the maximal tolerated dose of pramipexole for the treatment of depression when administered alone, a dose from 3 to 10 times higher than the maximal tolerated dose of pramipexole for the treatment of depression when administered alone, a dose from 4 to 10 times higher than the maximal tolerated dose of pramipexole for the treatment of depression when administered alone, and a dose from 6 to 10 times higher than the maximal tolerated dose of pramipexole for the treatment of depression when administered alone.

Advantageously, said NK1-antagonist Component (a) is selected from the group consisting of 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); described in U.S. Pat. No. 5,719,147, and in a liquid oral formulation, in US 2017/0035774, and in an injectable emulsion in a single-dose vial for intravenous use containing 130 mg aprepitant in 18 ml of emulsion (Cinvanti®), described in U.S. Pat. No. 9,808,465 (the contents of each disclosure is incorporated herein in its entirety by reference);

[3-{[(2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1-yl]phosphonic acid (fosaprepitant), disclosed, for example as meglumine salt in U.S. Pat. No. 5,691,336 and as di(cyclohexylamine) salt in US 2016/355533, the disclosures of which are incorporated herein in their entirety by reference;

(2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant) described in U.S. Pat. No. 7,294,630, the disclosure of which incorporated herein in its entirety by reference;

(2S)-1-[(3aS,4S,7aS)-4-hydroxy-4-(2-methoxyphenyl)-7,7-diphenyl-1,3,3a,5,6,7a-hexahydroisoindol-2-yl]-2-(2-methoxyphenyl)propan-1-one (INN: dapitant);

(2S,3S)—N-(5-tert-Butyl-2-methoxybenzyl)-2-(diphenylmethyl)-1-azabicyclo[2.2.2]octan-3-amine (maropitant), disclosed in U.S. Pat. No. 5,807,867, WO2005/082416 and EP 3173071 the contents of each of which are incorporated herein in its entirety by reference;

(2S,3S)-2-Diphenylmethyl-3-[(5-isopropyl-2-methoxybenzyl)amino]quinuclidine (eziopitant), disclosed by Evangelista S (2001). "Eziopitant. Pfizer"; Current Opinion in Investigational Drugs: 2 (10): 1441-3; reviewed in Drugs: the Investigational Drugs Journal 6 (8): 758-72;

(2S)—N-{2-[3,5-bis(trifluoromethyl)phenyl]ethyl}-2-[4-(cyclopropylmethyl)piperazin-1-yl]-N-methyl-2-phenylacetamide (INN figopitant);

N-[(2R)-1-[Acetyl-[(2-methoxyphenyl)methyl]amino]-3-(1H-indol-3-yl)propan-2-yl]-2-(4-piperidin-1-ylpiperidin-1-yl)acetamide (lanepitant);

2-[3,5-bis(trifluoromethyl)phenyl]-N,2-dimethyl-N-[4-(2-methylphenyl)-6-(4-methyl-1-piperazinyl)-3-pyridinyl]propanamide (netupitant) described in U.S. Pat. Nos. 6,297,375, 6,719,996 and 6,593,472, and, in an oral composition, comprising 300 mg of netupitant and palonosetron hydrochloride in an amount equivalent to 0.5 mg of palonosetron base, herein below referred to as "netupitant-300/palonosetron-0.5", 1 described in U.S. Pat. No. 8,951,969, the disclosures of which are incorporated herein in their entirety by reference;

{4-[5-{2-[3,5-bis(trifluoromethyl)phenyl]-N,2-dimethyl-propanamido}-4-(2-methylphenyl)pyridin-2-yl]-1-methylpiperazin-1-ium-1-yl}methyl hydrogen phosphate (INN: fosnetupitant), described in WO 2013/082102 and, in a pure crystalline form, in US 2017/0096442, available in an injectable composition, comprising 235 mg of fosnetupitant and palonosetron hydrochloride in an amount equivalent to 0.25 mg of palonosetron base (Akynzeo® for injection), herein below referred to as "netupitant-235palonosetron-0.25", the disclosures of which are incorporated herein in their entirety by reference;

(2R,4S)-4-[(8aS)-6-oxo-1,3,4,7,8,8a-hexahydropyrrolo[1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide maleate (orvepitant), described in U.S. Pat. Nos. 7,652,012 and 8,309,553, the disclosures of which are incorporated herein in their entirety by reference;

(5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615, the disclosures of which are incorporated herein in their entirety by reference;

3-((3aR,4R,5S,7aS)-5-[(1R)-1-[3,5-bis(trifluoromethylphenyl]ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731, the disclosures of which are incorporated herein in their entirety by reference;

2-(S)-(4-Fluoro-2-methyl-phenyl)-piperazine-1-carboxylic acid [1-(R)-(3,5-bis-trifluoromethyl-phenyl)-ethyl]-methyl-amide (vestipitant), described in WO 2001/25219 and, in intravenous formulation having a reduced tendency to cause hemolysis, in WO 2012/175434, the disclosure of which is incorporated herein in their entirety by reference; and (2S,3S)—N-[(2-methoxy-5-[5-(trifluoromethyl)tetrazol-1-yl]phenylmethyl]-2-phenylpiperidin-3-amine (GR2015171, vofopitant), described in U.S. Pat. No. 5,703,240 (see also U.S. Pat. No. 8,093,268) and also disclosed by Gardner C J et al. Regul Pept. 1996 Aug. 27; 65(1):45-53, the disclosures of which are incorporated herein in their entirety by reference;

and pharmaceutically acceptable salts of each of said NK1-antagonists.

Illustrative examples of pharmaceutically acceptable salts of basic advantageous NK1-antagonists include acid addition salts with mineral acids, such as hydrochloric acid, hydrobromic acid, hydriodic acid, sulfuric acid, phosphoric acid, nitric acid, carbonic acid, phosphoric acid and the like and acid addition salts with organic acids such as formic acid, acetic acid, propionic acid, oxalic acid, malonic acid, succinic acid, fumaric acid, maleic acid, lactic acid, malic acid, tartaric acid, citric acid, ascorbic acid, methanesulfonic acid, ethanesulfonic acid, gluconic acid, aspartic acid, glutamic acid. and the like.

Illustrative examples of pharmaceutically acceptable salts of acidic NK1-antagonists such as fosaprepitant include salts with inorganic bases such as alkaline metal or alkaline-earth metal salts, and salts with organic bases such as dicyclohexylamine salts, N-methyl-D-glucamine (meglumine) salts, and salts with amino acids, as described in U.S. Pat. No. 5,691,336, the contents of which is incorporated herein in its entirety by reference.

An advantageous NK1-antagonists to be used in combination with 6-propylamino-4,5,6,7-tetrahydro-1,3-benzothiazole-2-amine is selected from the group consisting of
aprepitant and pharmaceutically acceptable salts and solvates thereof,
fosaprepitant and pharmaceutically acceptable salts and solvates thereof,
casopitant and pharmaceutically acceptable salts and solvates thereof,
maropitant and pharmaceutically acceptable salts and solvates thereof,
eziopitant and pharmaceutically acceptable salts and solvates thereof,
lanepitant and pharmaceutically acceptable salts and solvates thereof,
netupitant and pharmaceutically acceptable salts and solvates thereof,
orvapitant and pharmaceutically acceptable salts and solvates thereof,
rolapitant and pharmaceutically acceptable salts and solvates thereof,
serlopitant and pharmaceutically acceptable salts and solvates thereof,
vestipitant and pharmaceutically acceptable salts and solvates thereof,
vofopitant and pharmaceutically acceptable salts and solvates thereof, and
netupitant-300/palonosetron-0.5.

Aprepitant, fosaprepitant meglumine, fosaprepitant di(cyclohexylamine), rolapitant, rolapitant hydrochloride and netupitant-300/palonosetron-0.5 are particularly advantageous NK1-antagonists.

Antagonists of the NK1 receptor that are approved for the prevention or treatment of postoperative nausea and vomiting or for the prevention of chemotherapy-induced nausea and vomiting are particularly useful according to the present invention. In particular, aprepitant is commercially available (Emend®) in capsules containing 40 mg, 80 mg, or 125 mg aprepitant or, as fosaprepitant dimeglumine (Emend® Injection), in vials containing 115 mg or 150 mg fosaprepitant; rolapitant is available (Varubi®) in 90-mg tablets; and netupitant is available (Akynzeo®) in a fixed-dose combination in capsules containing 300 mg of netupitant and 0.5 mg of the 5HT3-antagonist palonosetron (as hydrochloride), herein below referred to as "netupitant 300 mg/palonosetron 0.5 mg". Each of these preparations is a particularly advantageous NK1-antagonist Component (a) for the combination with pramipexole or pharmaceutically acceptable salts and solvates thereof Component (b) according to the present invention.

In the aforementioned method, use and combination, including fixed-dose combinations, said NK1-antagonist is present in an amount per unit form and is administered at a daily dose of 1 μg to 600 mg, normally from 1 mg to 600 mg, or from 1 mg to 300 mg.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant; netupitant and pharmaceutically acceptable salts and solvates thereof, at a daily dose equivalent to from 300 mg to 600 mg of netupitant; and netupitant-300/palonosetron-0.5.

Preferably, for said use in the treatment of depressive disorders, including MDD, in a patient, said NK1-antagonist Component (a) is aprepitant at a daily oral dose of from 10 mg to 250 mg; rolapitant, at a daily oral dose of from 30 mg to 270 mg or netupitant 300 mg/palonosetron 0.5 mg, orally administered once a day, each in combination with pramipexole or a pharmaceutically acceptable salt thereof Component (b) at a daily dose equivalent to from up to 10 times, from up to 4.7 times, or from 1.1 times to 10 times higher than the maximum recommended dose for the treatment of the motor symptoms of Parkinson's disease.

Preferably, for said use in the treatment of depressive disorders, including MDD, in a patient, said NK1-antagonist Component (a) is aprepitant at a daily oral dose of from 10 mg to 250 mg; rolapitant, at a daily oral dose of from 30 mg to 270 mg or netupitant 300 mg/palonosetron 0.5 mg, orally administered once a day, each in combination with pramipexole or a pharmaceutically acceptable salt thereof Component (b) at a daily dose equivalent to from 1.1 to 10 times higher than the maximal tolerated dose of pramipexole for the treatment of depression when administered alone. Such a daily dose includes, but is not limited to a dose from 1.1 to 10 times higher than the maximal tolerated dose of pramipexole for the treatment of depression when administered alone, a dose from 1.5 to 10 times higher than the maximal tolerated dose of pramipexole for the treatment of depression when administered alone, a dose from 2.5 to 10 times higher than the maximal tolerated dose of pramipexole for the treatment of depression when administered alone, a dose from 3 to 10 times higher than the maximal tolerated dose of pramipexole for the treatment of depression when administered alone, a dose from 4 to 10 times higher than the maximal tolerated dose of pramipexole for the treatment of depression when administered alone, and a dose from 6 to 10 times higher than the maximal tolerated dose of pramipexole for the treatment of depression when administered alone.

For its administration to a patient suffering from a depressive disorder, including MDD, in combination with pramipexole, each of the above NK1-antagonists is formulated in a pharmaceutical composition in dosage unit form comprising, as an active ingredient, said NK1-antagonist, in admixture with a pharmaceutical carrier or vehicle.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg of netupitant; and netupitant-300/palonosetron-0.5.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

As set forth above, by using a NK1-antagonist in combination with pramipexole or a pharmaceutically acceptable salt or solvate thereof, it is possible to treat a patient suffering from a MDD by maintaining an effective pramipexole or pharmaceutically acceptable salt or solvate thereof daily dose with minimal adverse effect.

Thus, in order to assure a sure, safe and concurrent administration of said NK1-antagonist and said pramipexole, the present invention provides a fixed-dose combination consisting of a pharmaceutical composition in dosage unit form comprising an effective amount per unit form of said NK1-antagonist and an effective amount per unit form of pramipexole, in admixture with a pharmaceutical carrier or vehicle.

These NK1-antagonist/pramipexole fixed-dose combinations are described in "The fourth aspect of the invention" section below.

The Pramipexole Component (b)

A stated in the Definitions, the term "pramipexole" generally stands for (S)-6-propylamino-4,5,6,7-tetrahydro-1,3-benzothiazole-2-amine, as free base (pramipexole) or as pharmaceutically acceptable salts and solvates thereof, including pramipexole dihydrochloride monohydrate, their doses per unit form and their daily doses being expressed as equivalents of pramipexole dihydrochloride monohydrate.

Pharmaceutically acceptable salts or solvates of pramipexole are also included in the present invention.

Illustrative examples of pharmaceutically acceptable salts of said pramipexole include acid addition salts with mineral acids such as hydrochloric acid, hydrobromic acid, hydriodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, tartaric acid, citric acid, carbonic acid, methanesulfonic acid, ethanesulfonic acid, aspartic acid, glutamic acid and the like. The solvation agent is generally water.

Among pramipexole and pharmaceutically acceptable salts or solvates thereof, pramipexole dihydrochloride monohydrate, commercially available, is preferred, but pramipexole base may be preferably used for some circumstance, for example in transdermal therapeutic systems. Stable pharmaceutical compositions comprising pramipexole dihydrochloride monohydrate, disclosed in WO 2012/0140604 and in WO 2008/122638, the contents of each of which are incorporated herein by reference in their entirety; and sustained release compositions comprising pramipexole dihydrochloride monohydrate, disclosed in U.S. Pat. No. 8,399,016, the contents of which is incorporated herein by reference in its entirety, may be useful for use in combination with a NK1-antagonist for the treatment of a depressive disorder, including MDD.

As set forth in the definitions, the effective daily dose of pramipexole is a dose equivalent to at least the pramipexole dihydrochloride monohydrate approved daily dose for the treatment of PD. Said daily approved dose is from 0.375 mg to 4.5 mg. However, it is hereby specified that, according to the present invention, the combination of a NK1-antagonist with said pramipexole allows the administration of pramipexole dihydrochloride monohydrate at daily doses as high as those approved for the treatment of Parkinson's disease without any adverse effect, but also allows the administration of pramipexole dihydrochloride monohydrate daily doses that are higher and also much higher than said approved doses. For example, the dose of pramipexole or a pharmaceutically acceptable salt thereof may be a daily dose equivalent to from up to 10 times, from up to 4.7 times, or from 1.1 times to 10 times higher than the maximum recommended dose for the treatment of the symptoms of Parkinson's disease (such as motor symptoms).

The effective daily dose of pramipexole may also be a dose equivalent to at least a maximal tolerated dose of pramipexole dihydrochloride monohydrate used for the treatment symptoms of PD (such as motor symptoms). For example, the effective daily dose of pramipexole or a pharmaceutically acceptable salt thereof may be a daily dose equivalent to from 1.1 to 10 times higher than a dose equivalent to at least a maximal tolerated dose of pramipexole dihydrochloride monohydrate used for the treatment of depression when administered alone. Such an effective daily dose, includes but is not limited to, a dose equivalent to a dose from 1.1 to 10 times higher than the maximal tolerated dose of pramipexole dihydrochloride monohydrate used for the treatment of depression when administered alone, a dose from 1.5 to 10 times higher than the maximal tolerated dose of pramipexole dihydrochloride monohydrate used for the treatment of depression when administered alone, a dose equivalent to a dose from 2.5 to 10 times higher than the maximal tolerated dose of pramipexole dihydrochloride monohydrate used for the treatment of depression when administered alone, a dose equivalent to a dose from 3 to 10 times higher than the maximal tolerated dose of pramipexole dihydrochloride monohydrate used for the treatment of depression when administered alone, a dose equivalent to a dose from 4 to 10 times higher than the maximal tolerated dose of pramipexole dihydrochloride monohydrate used for the treatment of depression when administered alone, and a dose equivalent to a dose from 6 to 10 times higher than the maximal tolerated dose of pramipexole dihydrochloride monohydrate used for the treatment of depression when administered alone.

For the treatment of depressive disorders, including MDD, in combination with a NK1-antagonist as described in "The NK1-antagonist Component (a)" section above, pramipexole is formulated in a pharmaceutical composition comprising said pramipexole in an amount equivalent to from 0.125 mg to 45 mg of pramipexole dihydrochloride monohydrate in admixture with a pharmaceutical carrier or vehicle. Said composition is administered to a patient in need of said treatment at daily dose of from 0.375 mg to 45 mg in combination with a NK1-antagonist at a daily dose of 1 µg to 600 mg, normally from 1 mg to 600 mg.

In particular, in said combination with a NK1-antagonist, pramipexole dihydrochloride monohydrate may be administered to a patient, including pediatric patients, suffering from a depressive disorder, including MDD, at a daily dose equivalent to from 0.375 mg to 45 mg, from more than 4.5 mg to 45 mg, from 5 mg to 45 mg, from more than 6 mg to 45 mg, from 10 mg to 45 mg, from 13 mg to 45 mg, or from 15 mg to 45 mg, normally from 0.375 mg to 21 mg, from more than 4.5 mg to 21 mg, from more than 6 mg to 21 mg, from 10 mg to 21 mg, from 13 mg to 21 mg, or from 15 mg to 21 mg of pramipexole dihydrochloride monohydrate; depending on the tolerability (in combination with the NK1-antagonist).

For its administration to a patient suffering from a depressive disorder, including MDD, in combination with an NK1-antagonist as described above in "The NK1-Antagonist Component (a)" section, the 6-propylamino-4,5,6,7-tetrahydro-1,3-benzothiazole-2-amine is formulated in a pharmaceutical composition in dosage unit form comprising, as an active ingredient, said 6-propylamino-4,5,6,7-tetrahydro-1,3-benzothiazole-2-amine, in admixture with a pharmaceutical carrier or vehicle.

According to the present invention, pramipexole or a pharmaceutically acceptable salt or solvate thereof, is in a pharmaceutical composition in dosage unit form comprising said pramipexole or a pharmaceutically acceptable salt or solvate thereof in an amount per unit form equivalent to from 0.125 mg to 45 mg of pramipexole dihydrochloride monohydrate.

For its use for the treatment of a depressive disorder, including MDD, in combination with a NK1-antagonist, pramipexole is formulated in a pharmaceutical composition in dosage unit form comprising said pramipexole in an amount per IR- or ER-form (including low doses to be used during the titration period) equivalent to from 0.125 mg to 45 mg, advantageously from more than 4.5 mg to 45 mg, from more than 6 mg to 45 mg, from 10 mg to 45 mg, from 13 mg to 45 mg, or from 15 mg to 45 mg of pramipexole dihydrochloride monohydrate.

In particular, said pharmaceutical composition Component (b) comprises, as an active ingredient, pramipexole or a pharmaceutically acceptable salt thereof in an amount per unit form equivalent to from 0.125 mg to 22.5 mg, normally from 1.5 mg to 22.5 mg, from more than 3 mg to 22.5 mg, from 5 mg to 22.5 mg, from 6.5 mg to 22.5 mg, or from 7.5 mg to 22.5 mg of pramipexole dihydrochloride monohydrate, in an IR-formulation, or in an amount per unit form equivalent to from 0.375 mg to 45 mg, from more than 4.5 mg to 45 mg, from 5 mg to 45 mg, from more than 6 mg to 45 mg, from 10 mg to 45 mg from 13 mg to 45 mg, or from 15 mg to 45 mg of pramipexole dihydrochloride monohydrate in an ER-formulation. Said amounts per unit form include low amounts for use of said unit forms during the titration period.

In a preferred embodiment, in order to provide the treatment of a depressive disorder, including MDD, with high pramipexole doses, the invention provides a pharmaceutical composition in dosage unit form comprising, as an active ingredient, pramipexole or a pharmaceutically acceptable salts or solvates thereof in an amount per unit form equivalent to from 15 mg to 45 mg, from 15 mg to 30 mg, or from 15 mg to 21 mg of pramipexole dihydrochloride monohydrate, in admixture with a pharmaceutical carrier or vehicle.

As set forth above, a NK1-antagonist, in combination with pramipexole or a pharmaceutically acceptable salt or solvate thereof, can be used to treat a patient suffering from a depressive disorder, including MDD, by maintaining a therapeutically effective pramipexole or pharmaceutically acceptable salt or solvate thereof daily dose with minimal adverse effect.

In order to provide concurrent administration of said NK1-antagonist and of said pramipexole or pharmaceutically acceptable salt or solvate thereof, the invention also provides a fixed-dose combination comprising a pharmaceutical composition in dosage unit form comprising, as active ingredients, a NK1-antagonist; and pramipexole or pharmaceutically acceptable salts and solvates thereof, in admixture with a pharmaceutical carrier or vehicle.

The NK1-antagonist pramipexole fixed-dose combinations will be described in "The Pharmaceutical Compositions" section below.

First Aspect of the Invention

According to a first aspect, the present invention includes a method for safely treating a depressive disorder, including MDD, in patients suffering from a depressive disorder, with pramipexole by concurrently administering to said patients a NK1-antagonist.

More particularly, the invention provides a method for treating a patient suffering from a depressive disorder, including MDD, which comprises administering to a patient in need of said treatment an effective dose of said NK1-antagonist in combination with an effective daily dose of pramipexole or a pharmaceutically acceptable salt thereof.

According to a preferred embodiment,
said NK1-antagonist is selected from the group consisting of aprepitant and pharmaceutically acceptable salts and solvates thereof, fosaprepitant and pharmaceutically acceptable salts and solvates thereof, rolapitant and pharmaceutically acceptable salts and solvates thereof, netupitant and pharmaceutically acceptable salts and solvates thereof, and netupitant-300/palonosetron-0.5; each at a daily dose described in "The NK1-antagonist Component (a)" section, except for netupitant-300/palonosetron-0.5 which is provided once a day or every 2-4 days; and
said pramipexole or pharmaceutically acceptable salts or solvates thereof is administered at a daily dose as described above in "The pramipexole Component (b)" section.

According to an advantageous embodiment, in the method of the present invention the NK1-antagonist is aprepitant, fosaprepitant meglumine, or rolapitant and the pramipexole or a pharmaceutically acceptable salt or solvate thereof is pramipexole dihydrochloride monohydrate, each at the daily doses described in the respective sections.

In carrying out the method of the present invention, the daily dose of these NK1-antagonists is at least as high as that for preventing or treating nausea and vomiting in patients undergoing a surgical operation or cancer chemotherapy according to the current protocols for said treatment or prevention. Said daily dose is from 1 µg to 600 mg, normally from 1 mg to 600 mg, or from 1 mg to 300 mg.

The pramipexole or a pharmaceutically acceptable salt or solvate thereof daily dose is equivalent to from 0.375 mg to 45 mg of pramipexole dihydrochloride monohydrate, including daily doses used during the titration period.

A NK1-antagonist selected from the group consisting of aprepitant and pharmaceutically acceptable salts and solvates thereof and rolapitant and pharmaceutically acceptable salt and solvate thereof is a particularly advantageous NK1-antagonist.

Preferably, in said combination, said NK1-antagonist is aprepitant and said pramipexole or a pharmaceutically acceptable salt or solvate thereof is pramipexole dihydrochloride monohydrate.

In particular, said NK1-antagonist in said combination is aprepitant, at an effective daily dose of from 10 mg to 250 mg and said pramipexole or pharmaceutically acceptable salt or solvate thereof in said combination is pramipexole dihydrochloride monohydrate, at an effective daily dose in a range selected from the group consisting of from more than 4.5 mg to 45 mg, from 5 mg to 45 mg, from more than 6 mg to 45 mg, from 10 mg to 45 mg, from 13 mg to 45 mg, or from 15 mg to 45 mg.

In carrying out the method (or use) of the present invention, said NK1-antagonist and said pramipexole or pharmaceutically acceptable salt or solvate thereof are each formulated in a pharmaceutical composition in dosage unit form comprising, respectively, said NK1-antagonist and said pramipexole or pharmaceutically acceptable salt or solvate thereof, each in admixture with a pharmaceutical carrier or vehicle.

Said NK1-antagonist and said pramipexole or pharmaceutically acceptable salt or solvate thereof may also be in a fixed-dose combination, co-formulated in a pharmaceutical composition in dosage unit form comprising an effective amount per unit form of said NK1-antagonist, and an effective amount per unit form of said pramipexole or pharmaceutically acceptable salts and solvates thereof, in admixture with a pharmaceutical carrier or vehicle. This fixed dose combination will be described herein below in the fourth aspect of the invention.

The doses per unit form of said NK1-antagonist and of said pramipexole are described above, respectively, in "The NK1-antagonist Component (a)" and in "The pramipexole Component (b)" sections.

In particular, in said composition, said NK1-antagonist is present in an amount per unit form of from 1 µg to 600 mg or from 1 mg to 600 mg.

In said composition said pramipexole or pharmaceutically acceptable salt or solvate thereof is present in an amount per unit form equivalent to from 0.125 mg to 45 mg or from 0.125 mg to 21 mg of pramipexole dihydrochloride monohydrate.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; and netupitant-300/palonosetron-0.5. Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

Said pramipexole dose per unit form consists of or includes an amount per unit form equivalent to a range selected from the group consisting of from 0.125 mg to 45 mg, from more than 4.5 mg to 45 mg, from 5 mg to 45 mg, from more than 6 mg to 45 mg, from 10 mg to 45 mg, from 13 mg to 45 mg, and from 15 mg to 45 mg of pramipexole dihydrochloride monohydrate.

According to an embodiment, in the method of the present invention the NK1-antagonist is aprepitant or rolapitant, and pramipexole or a pharmaceutically acceptable salt or solvate thereof is administered at a daily dose that is equivalent to from up to 10 times, from up to 4.7 times, or from 1.1 times to 10 times higher than the maximum recommended pramipexole dihydrochloride monohydrate dose approved for the relief of the symptoms of PD (such as motor symptoms).

According to another embodiment, in the method of the present invention the NK1-antagonist is aprepitant or rolapitant, and pramipexole or a pharmaceutically acceptable salt or solvate thereof is administered at a daily dose that is equivalent to a dose from 1.1 times to 10 times higher than a maximal tolerated dose of pramipexole dihydrochloride monohydrate dose for the treatment of depression when administered alone. Such a daily dose, includes but is not limited to, a daily dose that is equivalent to a dose from 1.1 to 10 times higher than the maximal tolerated dose of pramipexole dihydrochloride monohydrate dose for the treatment of depression when administered alone, a dose from 1.5 to 10 times higher than the maximal tolerated dose of pramipexole dihydrochloride monohydrate dose for the treatment of depression when administered alone, a daily dose that is equivalent to a dose from 2.5 to 10 times higher than the maximal tolerated dose of pramipexole dihydrochloride monohydrate dose for the treatment of depression when administered alone, a daily dose that is equivalent to a dose from 3 to 10 times higher than the maximal tolerated dose of pramipexole dihydrochloride monohydrate dose for the treatment of depression when administered alone, a daily dose that is equivalent to a dose from 4 to 10 times higher than the maximal tolerated dose of pramipexole dihydrochloride monohydrate dose for the treatment of depression when administered alone, and a daily dose that is equivalent to a dose from 6 to 10 times higher than the maximal tolerated dose of pramipexole dihydrochloride monohydrate dose for the treatment of depression when administered alone.

According to this embodiment, in said method (or use), said NK1-antagonist, at the aforementioned effective daily dose, is administered to said patient, in combination with pramipexole or a pharmaceutically acceptable salt or solvate thereof administered to said patient at a daily dose equivalent to from more than 4.5 mg to 21 mg, normally from more than 6 mg to 21 mg, from 10 mg to 21 mg, from 13 mg to 21 mg or from 15 mg to 21 mg of pramipexole dihydrochloride monohydrate.

Preferably, according to this embodiment, in the method for treating a depressive disorder, including MDD, in an adult patient according to the present invention, said NK1-antagonist is aprepitant, at a daily oral dose of from 10 mg to 250 mg; or rolapitant, at a daily oral dose of from 30 mg to 270 mg, in combination with pramipexole or a pharmaceutically acceptable salt or solvate thereof, at an effective daily oral dose corresponding to from more than 4.5 mg to 21 mg, normally from more than 6 mg to 21 mg, from 10 mg to 21 mg, from 13 mg to 21 mg, or from 15 mg to 21 mg of pramipexole dihydrochloride monohydrate.

Second Aspect of the Invention

According to a second aspect, the invention provides a NK1-antagonist for use in combination with pramipexole or a pharmaceutically acceptable salt or solvate thereof for the treatment of a depressive disorder, including MDD, in a patient in need of said treatment.

In particular, this second aspect of the present invention provides
(a) a NK1-antagonist, in combination with
(b) pramipexole or a pharmaceutically acceptable salt or solvate thereof, at a dose level (in pramipexole dihydrochloride monohydrate) that is from up to 10 times, from up to 4.7 times, or from 1.1 times to 10 times higher than the maximum pramipexole dihydrochloride monohydrate daily dose recommended for the relief of the symptoms of Parkinson's disease (such as motor symptoms),
for use for the treatment of depressive disorder, including MDD, in a patient.

Any of the NK1-antagonists described in "The NK1-antagonist Component (a)" section may be used, normally in a dosage unit form, according to this second aspect of the invention.

In particular, this second aspect of the present invention provides a NK1-antagonist, in an amount per unit form of from 1 µg to 600 mg, normally from 1 mg to 600 mg or from 1 mg to 300 mg, for use in combination with a daily dose of said pramipexole or pharmaceutically acceptable salt or solvate thereof (including low doses used in the titration period) equivalent to from 0.375 mg to 45 mg of pramipexole dihydrochloride monohydrate, for the treatment of a depressive disorder, including MDD, in a patient in need of said treatment.

For the use according to this second aspect of present invention, the daily dose of said NK1-antagonist is at least as high as that for preventing or treating nausea and vomiting in patients undergoing a surgical operation or cancer chemotherapy according to the current protocols for said treatment or prevention. Said daily dose will range from 1 µg to 600 mg, normally from 1 mg to 600 mg or from 1 mg to 300 mg.

For its use for the treatment of a depressive disorder, including MDD, according to the present invention, the NK1-antagonist, at the aforementioned effective daily dose, as described in "The NK1-antagonist Component (a)" section, is administered to a patient in need of said treatment in combination with pramipexole at the aforementioned effective daily dose, as described in "The pramipexole Component (b)" section.

Normally, for its use according to this second aspect, the invention provides said NK1-antagonist Component (a), in a pharmaceutical composition comprising, as an active ingredient, said NK1-antagonist, in admixture with a pharmaceutical carrier or vehicle, for use for the treatment of a depressive disorder, including MDD, in a patient, in combination with pramipexole or a pharmaceutically acceptable salt or solvate thereof Component (b), also in a pharmaceutical composition, in admixture with a pharmaceutical carrier or vehicle, to be administered to said patient at a daily dose that is equivalent to from up to 10 times, from up to 4.7 times, or from 1.1 times to 10 times higher than the maximum pramipexole dihydrochloride monohydrate daily dose recommended for the relief of the motor symptoms of Parkinson's disease (such a motor symptoms).

As another use according to this second aspect, the invention provides NK1-antagonist Component (a), in a pharmaceutical composition comprising, as an active ingredient, said NK-1 antagonist, in admixture with a pharmaceutical carrier or vehicle, for the use of the treatment of a depressive disorder, including MDD, in a patient, in combination with pramipexole or a pharmaceutically acceptable salt or solvate thereof Component (b), also in a pharmaceutical composition, in admixture with a pharmaceutical carrier or vehicle, to be administered to said patient at a daily dose that is equivalent to a dose from 1.1 times to 10 times higher than a maximal tolerated dose of pramipexole dihydrochloride monohydrate dose for the treatment of depression when administered alone. Such a daily dose, includes but is not limited to, a daily dose that is equivalent to a dose from 1.1 to 10 times higher than the maximal tolerated dose of pramipexole dihydrochloride monohydrate dose for the treatment of depression when administered alone, a daily dose that is equivalent to a dose from 1.5 to 10 times higher than the maximal tolerated dose of pramipexole dihydrochloride monohydrate dose for the treatment of depression when administered alone, a daily dose that is equivalent to a dose from 2.5 to 10 times higher than the maximal tolerated dose of pramipexole dihydrochloride monohydrate dose for the treatment of depression when administered alone, a daily dose that is equivalent to a dose from 3 to 10 times higher than the maximal tolerated dose of pramipexole dihydrochloride monohydrate dose for the treatment of depression when administered alone, a daily dose that is equivalent to a dose from 4 to 10 times higher than the maximal tolerated dose of pramipexole dihydrochloride monohydrate dose for the treatment of depression when administered alone, and a daily dose that is equivalent to a dose from 6 to 10 times higher than the maximal tolerated dose of pramipexole dihydrochloride monohydrate dose for the treatment of depression when administered alone.

Said pharmaceutical composition in dosage unit form comprises said NK1-antagonist Component (a), in an amount of from 1 µg to 600 mg, in admixture with a pharmaceutical carrier or vehicle, and is for use for the treatment of a depressive disorder, including MDD, in a patient, in combination with pramipexole or a pharmaceutically acceptable salt or solvate thereof Component (b), in doses, in pramipexole dihydrochloride monohydrate, from up to 10 times, from up to 4.7 times, or from 1.1 times to 10 times higher than the daily dose approved for the relief of the symptoms of PD (such as motor symptoms).

Said pharmaceutical composition in dosage unit form comprises said NK1-antagonist Component (a), in an amount of from 1 µg to 600 mg, in admixture with a pharmaceutical carrier or vehicle, and is for use for the treatment of a depressive disorder, including MDD, in a patient, in combination with pramipexole or a pharmaceutically acceptable salt or solvate thereof Component (b), in doses, in pramipexole dihydrochloride monohydrate, from 1.1 times to 10 times higher than a maximal tolerated dose of pramipexole dihydrochloride monohydrate dose for the treatment of depression when administered alone. Such a dose, includes but is not limited to, a daily dose that is equivalent to a dose from 1.1 to 10 times higher than the maximal tolerated dose of pramipexole dihydrochloride monohydrate dose for the treatment of depression when administered alone, a daily dose that is equivalent to a dose from 1.5 to 10 times higher than the maximal tolerated dose of pramipexole dihydrochloride monohydrate dose for the treatment of depression when administered alone, a daily dose that is equivalent to a dose from 2.5 to 10 times higher than the maximal tolerated dose of pramipexole dihydrochloride monohydrate dose for the treatment of depression when administered alone, a daily dose that is equivalent to a dose from 3 to 10 times higher than the maximal tolerated dose of pramipexole dihydrochloride monohydrate dose for the treatment of depression when administered alone, a daily dose that is equivalent to a dose from 4 to 10 times higher than the maximal tolerated dose of pramipexole dihydrochloride monohydrate dose for the treatment of depression when administered alone, and a daily dose that is equivalent to a dose from 6 to 10 times higher than the maximal tolerated dose of pramipexole dihydrochloride monohydrate dose for the treatment of depression when administered alone.

According to an embodiment, said NK1-antagonist, in an amount per unit form of from 1 μg to 600 mg, is for use in the treatment of a depressive disorder, including MDD, in a patient in combination with a pramipexole, also in a pharmaceutical composition in dosage unit form comprising said pramipexole in an amount per unit form equivalent to from 0.125 mg to 45 mg, from more than 4.5 mg to 45 mg, from more than 6 mg to 45 mg, from 10 mg to 45 mg, from 13 mg to 45 mg, or from 15 mg to 45 mg of pramipexole dihydrochloride monohydrate, to be administered to said patient at a daily dose equivalent to from 0.375 mg to 45 mg, from more than 4.5 mg to 45 mg, from more than 6 mg to 45 mg, from 10 mg to 45 mg, from 13 mg to 45 mg, or from 15 mg to 45 mg of pramipexole dihydrochloride monohydrate.

In particular, said NK1-antagonist is selected from the group consisting of aprepitant and pharmaceutically acceptable salts and solvates thereof, in an amount per unit form equivalent to from 10 mg to 250 of aprepitant; fosaprepitant and pharmaceutically acceptable salts and solvates thereof, in an amount per unit form equivalent to from 10 mg to 250 of aprepitant; rolapitant and pharmaceutically acceptable salts and solvates thereof, in an amount per unit form equivalent to from 15 mg to 270 mg of rolapitant; netupitant and pharmaceutically acceptable salts and solvates thereof, in an amount per unit form equivalent to from 300 mg to 600 mg; and netupitant-300/palonosetron-0.5.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

Pramipexole, in said combination, may be formulated in a pharmaceutical composition in IR- or ER-form, in an amount per unit form as described in "The pramipexole Component (b)" section and administered twice to three times per day in an IR-formulation or once a day in an ER-formulation, at the aforementioned daily doses, in combination with the NK1-antagonist.

Third Aspect of the Invention

According to this third aspect, the present invention provides the use of a NK1-antagonist for the preparation of a medicament for the treatment of a depressive disorder, including MDD, in a patient in need of said treatment, in combination with pramipexole or a pharmaceutically acceptable salt or solvate thereof.

This third aspect of the invention provides the use of said NK1-antagonist Component (a), for the preparation of a medicament consisting of a pharmaceutical composition comprising, as an active ingredient, said NK1-antagonist, in an amount of from 1 μg to 600 mg, in admixture with a pharmaceutical carrier or vehicle, for the treatment of a depressive disorder, including MDD, in a patient, in combination with pramipexole or a pharmaceutically acceptable salt or solvate thereof Component (b), at a daily dose, (in pramipexole dihydrochloride monohydrate) from up to 10 times, from up to 4.7 times, or from 1.1 times to 10 times higher than the daily dose approved for the relief of the symptoms of PD (such as motor symptoms).

This third aspect of the invention also provides the use of said NK1-antagonist Component (a), for the preparation of a medicament consisting of a pharmaceutical composition comprising, as an active ingredient, said NK1-antagonist, in an amount of from 1 μg to 600 mg, in admixture with a pharmaceutical carrier or vehicle, for the treatment of a depressive disorder, including MDD, in a patient, in combination with pramipexole or a pharmaceutically acceptable salt or solvate thereof Component (b), at a daily dose, (in pramipexole dihydrochloride monohydrate) from 1.1 times to 10 times higher than a maximal tolerated dose of pramipexole dihydrochloride monohydrate dose for the treatment of depression when administered alone. Such a daily dose, includes but is not limited to, a daily dose that is equivalent to a daily dose that is equivalent to a dose from 1.1 to 10 times higher than the maximal tolerated dose of pramipexole dihydrochloride monohydrate dose for the treatment of depression when administered alone, a dose from 1.5 to 10 times higher than the maximal tolerated dose of pramipexole dihydrochloride monohydrate dose for the treatment of depression when administered alone, a daily dose that is equivalent to a dose from 2.5 to 10 times higher than the maximal tolerated dose of pramipexole dihydrochloride monohydrate dose for the treatment of depression when administered alone, a daily dose that is equivalent to a dose from 3 to 10 times higher than the maximal tolerated dose of pramipexole dihydrochloride monohydrate dose for the treatment of depression when administered alone, a daily dose that is equivalent to a dose from 4 to 10 times higher than the maximal tolerated dose of pramipexole dihydrochloride monohydrate dose for the treatment of depression when administered alone, and a daily dose that is equivalent to a dose from 6 to 10 times higher than the maximal tolerated dose of pramipexole dihydrochloride monohydrate dose for the treatment of depression when administered alone.

For this use, said NK1-antagonist is formulated in a medicament consisting of or comprising a pharmaceutical composition in dosage unit form to be administered to a patient suffering from a depressive disorder, including MDD, in combination with pramipexole or a pharmaceutically acceptable salt or solvate thereof, also in a pharmaceutical composition in dosage unit form.

The above medicament consisting of or comprising combinations of pharmaceutical compositions, for use for the treatment of depressive disorder, including MMD, in a patient, normally are in dosage unit form, in an IR or ER formulation, and each of said compositions may comprise
(a) said NK1-antagonist, in admixture with a pharmaceutical carrier or vehicle, and/or
(b) said pramipexole or pharmaceutically acceptable salt or solvate thereof, in admixture with a pharmaceutical carrier or vehicle, or
(a/b) both said NK1-antagonist and said pramipexole or pharmaceutically acceptable salt or solvate thereof, in a fixed-dose combination comprising said NK1-antagonist and said pramipexole or pharmaceutically acceptable salt or solvate thereof in admixture with a pharmaceutical carrier or vehicle.

These medicament consisting of or comprising combinations of pharmaceutical compositions, each pharmaceutical composition comprising Component (a) and/or Component (b) or the (a/b)-fixed-dose combination, are useful and for use for the treatment of depressive disorder, including MMD, in a patient.

Thus, this third aspect of the invention provides the use of a NK1-antagonist for the preparation of a pharmaceutical composition in dosage unit form comprising, as an active ingredient in admixture with a pharmaceutical carrier or vehicle, said NK1-antagonist in an amount per unit form of form 1 µg to 600 mg (for use) for the treatment of a depressive disorder, including MDD, in a patient in need of said treatment, in combination with pramipexole, also in a pharmaceutical composition in dosage unit form comprising, in admixture with a pharmaceutical carrier or vehicle, said pramipexole in an amount per unit form equivalent to from 0.125 mg to 45 mg of pramipexole dihydrochloride monohydrate, to be administered to said patient at a daily dose equivalent to from 0.375 mg to 45 mg of pramipexole dihydrochloride monohydrate.

As set forth above, the above pramipexole dose-range (daily and per unit form) includes low doses to be used during the titration period.

In particular, in said pharmaceutical combination,
(a) said NK1-antagonist is present in said composition in an amount per unit form of from 1 µg to 600 mg, to be administered at a daily dose of from 1 mg to 600 mg; and
(b) said pramipexole Component (b) is present in said composition in an amount per unit form equivalent to from 0.125 mg to 45 mg, from more than 4.5 mg to 45 mg, from more than 6 mg to 45 mg, from 10 mg to 45 mg, from 13 mg to 45 mg, or from 15 mg to 45 mg, to be administered at a daily dose equivalent to from 0.375 mg to 45 mg, preferably from more than 4.5 mg to 45 mg, from more than 6 mg to 45 mg, from 10 mg to 45 mg, from 13 mg to 45 mg, or from 15 mg to 45 mg of pramipexole dihydrochloride monohydrate.

According to an embodiment of this third aspect, the invention provides a medicament consisting of or comprising a pharmaceutical combination comprising, as Components, Component (a) a NK1-antagonist, in a pharmaceutical composition in dosage unit form comprising, as an active ingredient, said NK1-antagonist, in an amount per unit form of from 1 mg to 600 mg, in admixture with a pharmaceutical carrier or vehicle; and Component (b) pramipexole or a pharmaceutically acceptable salt or solvate thereof, in a pharmaceutical composition in dosage unit form comprising, as an active ingredient, said pramipexole or a pharmaceutically acceptable salt or solvate thereof, in an amount per unit form equivalent to from 0.125 mg to 21 mg of pramipexole dihydrochloride monohydrate, in admixture with a pharmaceutical carrier or vehicle.

The pharmaceutical combination according to this third aspect of the invention may be administered to patients suffering from a depressive disorder, including MDD, with the intent of finding and adopting a safe and effective pramipexole daily dose with higher therapeutic efficacy than is used or known in the art, for the heretofore unachieved treatment or alleviation of symptoms of said depressive disorder, including MDD, in each patient. Normally, Component (a) and Component (b) are concurrently or sequentially administered to said patient suffering from a depressive disorder, including MDD.

Any of the aforementioned NK1-antagonists may be used as an active ingredient of the pharmaceutical composition Component (a) of the combination according to this third aspect of the invention. Preferably, said NK1-antagonist is selected from the group consisting of aprepitant, in an amount per unit form of from 10 mg to 250 mg; fosaprepitant dimeglumine, in an amount per unit form of from 10 mg to 150 mg, rolapitant, in an amount per unit form of from 30 mg to 270 mg and netupitant, in an amount per unit form of from 100 mg to 600 mg. If said NK1-antagonist is netupitant, in an amount per unit form of from 100 mg to 600 mg, the above pharmaceutical composition Component (a) may also comprise, as a second active ingredient, palonosetron or a pharmaceutically acceptable salt thereof, in an amount per unit form equivalent to from 0.1 mg to 0.5 mg of palonosetron base.

In the pharmaceutical composition Component (b), pramipexole or pharmaceutically acceptable salt or solvate thereof, is in an amount per unit form equivalent to from 0.125 mg to 45 mg, in particular from more than 4.5 mg to 45 mg, from more than 6 mg to 45 mg, from 10 mg to 45 mg, from 13 mg to 45 mg, or from 15 mg to 45 mg of pramipexole dihydrochloride monohydrate.

In particular, the dose of pramipexole or pharmaceutically acceptable salt or solvate thereof per IR-unit form, for the treatment of a depressive disorder, including MDD, will range from an amount equivalent to from 0.125 mg to 22.5 mg, from 1.5 to 22.5 mg, from more than 3 mg to 22.5 mg, from 5 mg to 22.5 mg, from 6.5 mg to 22.5 mg, or from 10 mg to 22.5 mg of pramipexole dihydrochloride monohydrate, depending on safety and tolerability (in combination with the NK1-antagonist).

The dose per unit form of pramipexole or pharmaceutically acceptable salt or solvate thereof in an ER formulation, including slow-release compositions and transdermal therapeutic systems such as transdermal patches, for the treatment of a depressive disorder, including MDD, will range from an amount that is equivalent to from 0.375 mg to 45 mg, from 5 mg to 45 mg, from more than 6 mg to 45 mg, from 10 mg to 45 mg from 13 mg to 45 mg, or from 15 mg to 45 mg of pramipexole dihydrochloride monohydrate, depending on the tolerability (in combination with said NK1-antagonist).

According to an embodiment, in the pharmaceutical composition Component (b), pramipexole or pharmaceutically acceptable salt or solvate thereof, is in an amount per unit form equivalent to from 0.125 mg to 21 mg, in particular from 0.125 mg to less than 1.6 mg, from 1.6 mg to 21 mg, from more than 4.5 mg to 21 mg or from more than 6 mg to 21 mg of pramipexole dihydrochloride monohydrate.

In particular, according to this embodiment the dose of pramipexole or pharmaceutically acceptable salt or solvate thereof per IR-unit form, for the treatment of a depressive disorder, including MDD, will range from an amount equivalent to from 1.6 mg to 10.5 mg, from 1.8 to 10.5 mg, from 2.4 mg to 10.5 mg or from 3 mg to 10.5 mg of pramipexole dihydrochloride monohydrate, depending on safety and tolerability (in combination with the NK1-antagonist).

The dose per unit form of pramipexole or pharmaceutically acceptable salt or solvate thereof in an ER formulation, including slow-release compositions and transdermal therapeutic systems such as transdermal patches, for the treatment of a depressive disorder, including MDD, according to this embodiment, will range from an amount that is equivalent to from more than 4.5 mg to 21 mg, in particular from 4.8 mg to 21 mg, or from more than 6 mg to 21 mg of pramipexole dihydrochloride monohydrate, depending on the tolerability (in combination with said NK1-antagonist).

In the case of separate (concurrent or sequential) administration of said NK1-antagonist, in an effective amount per unit form, and of said pramipexole, in an effective amount per unit form, each of them can be packaged in a kit comprising said NK1-antagonist, in admixture with a pharmaceutical carrier or vehicle, in a container; and said pramipexole, in admixture with a pharmaceutical carrier or vehicle, in another, separate container.

For the intended use in the treatment of a depressive disorder, including MDD, in combination with pramipexole, the NK1-antagonist is formulated in a pharmaceutical composition, wherein said NK1-antagonist is in admixture with a pharmaceutical carrier or vehicle.

For their concurrent administration for the treatment of depressive disorder, including MDD, said NK1-antagonist and said pramipexole may also be formulated together and with a pharmaceutical carrier or vehicle, in a pharmaceutical composition (fixed-dose combination).

Fourth Aspect of the Invention

A fourth aspect of the present invention provides the use of a NK1-antagonist for the manufacture of a medicament for the treatment of a depressive disorder, including MDD, as a fixed-dose combination consisting of or comprising a pharmaceutical composition in dosage unit form which comprises, as an active ingredient, said NK1-antagonist, in an effective amount per unit form, and, as another active ingredient, pramipexole or a pharmaceutically acceptable salt thereof, in an effective amount per unit form, in admixture with a pharmaceutical carrier or vehicle;

the use of a NK1-antagonist for the manufacture of a medicament for the treatment of a depressive disorder, including MDD, as a fixed-dose combination consisting or consisting essentially of a pharmaceutical composition in dosage unit form which comprises, as an active ingredient, said NK1-antagonist, in an effective amount per unit form, in admixture with a pharmaceutical carrier or vehicle; and, a pharmaceutical composition in dosage unit form which comprises, as an active ingredient, pramipexole or a pharmaceutically acceptable salt thereof, in an effective amount per unit form, in admixture with a pharmaceutical carrier or vehicle; said medicament as a fixed dose combination for use in the treatment of a depressive disorder, including MDD; and a method for treating a depressive disorder, including MDD, in a patient in need of said treatment which comprises administering to said patient said medicament as a fixed-dose combination.

For this method (or use), the invention provides a medicament as a fixed-dose combination consisting of or comprising a pharmaceutical composition in dosage unit form which comprises (a) a NK1-antagonist, in an amount per unit form of from 1 µg to 600 mg; and (b) pramipexole or a pharmaceutically acceptable salt thereof, in an amount equivalent to from 0.125 mg to 45 mg of pramipexole dihydrochloride monohydrate, in admixture with a pharmaceutical carrier or vehicle, for use in the treatment of a depressive disorder, including MDD, in a patient in need of said treatment.

According to this embodiment of the fourth aspect of the invention, any of the NK1-antagonists described in "The NK1-antagonist Component (a)" section may be used as Component (a) of said pharmaceutical composition, in an amount per unit form as described in said section, in a fixed dose combination with pramipexole Component (b) in an amount per unit form as described above in "The pramipexole Component (b)" section, in admixture with a pharmaceutical carrier or vehicle.

For this method (or use), the invention provides a medicament as a fixed-dose combination consisting of or comprising (a) a pharmaceutical composition in dosage unit form which comprises a NK1-antagonist, in an amount per unit form of from 1 µg to 600 mg, in admixture with a pharmaceutical carrier or vehicle; and (b) a pharmaceutical composition in dosage unit form which comprises pramipexole or a pharmaceutically acceptable salt thereof, in an amount equivalent to from 0.125 mg to 45 mg of pramipexole dihydrochloride monohydrate, in admixture with a pharmaceutical carrier or vehicle;

for use in the treatment of a depressive disorder, including MDD, in a patient in need of said treatment.

According to this embodiment, any of the NK1-antagonists described in "The NK1-antagonist Component (a)" section may be used in pharmaceutical composition (a), in an amount per unit form as described in said section, and pramipexole as described above in "The pramipexole Component (b)" section may be used in pharmaceutical composition (b) in an amount per unit form as described therein.

According to an embodiment, said NK1-antagonist Component (a) or NK-1 antagonist in pharmaceutical composition (a) is selected from the group consisting of aprepitant and pharmaceutically acceptable salts and solvates thereof, in an amount per unit form equivalent to from 10 mg to 250 mg of aprepitant; fosaprepitant and pharmaceutically acceptable salts and solvates thereof, in an amount per unit form equivalent to from 10 mg to 250 mg of aprepitant; rolapitant and pharmaceutically acceptable salts and solvates thereof, in an amount per unit form equivalent to from 15 mg to 270 mg of rolapitant; and netupitant and pharmaceutically acceptable salts and solvates thereof, in an amount, per unit form, equivalent to from 300 mg to 600 mg; and said pramipexole Component (b) or pramipexole in pharmaceutical composition (b) is in an amount per unit form equivalent to a range selected from the group consisting of from 0.125 mg to 45 mg, from more than 4.5 mg to 45 mg, from more than 6 mg to 45 mg, from 10 mg to 45 mg, from 13 mg to 45 mg, and from 15 mg to 45 mg of pramipexole dihydrochloride monohydrate.

In pharmaceutical compositions described herein, the NK1-antagonist normally is in an IR-unit form and said pramipexole may be in an IR-unit form or, preferably, in an ER-unit form. Said unit forms are described in "The formulations" section below.

According to an embodiment, said fixed-dose combination comprises or consists of a pharmaceutical composition comprising (a) said NK1-antagonist, in an amount/unit form of from 1 µg to 600 mg; and (b) pramipexole or a pharmaceutically acceptable salt or solvate thereof, in an amount per unit form equivalent to from 0.125 mg to 21 mg, in admixture with a pharmaceutical carrier or vehicle, and is for use for the treatment of depressive disorder, including MDD, in a patient.

According to an embodiment, said fixed-dose combination comprises or consists of (a) a pharmaceutical composition comprising said NK1-antagonist, in an amount/unit form of from 1 μg to 600 mg, in admixture with a pharmaceutical carrier or vehicle; and
(b) a pharmaceutical composition comprising pramipexole or a pharmaceutically acceptable salt or solvate thereof, in an amount per unit form equivalent to from 0.125 mg to 21 mg, in admixture with a pharmaceutical carrier or vehicle;

for use for the treatment of depressive disorder, including MDD, in a patient.

According to this embodiment, for said uses and method, in the fixed-dose combination said NK1-antagonist, in an amount of from 1 μg to 600 mg, normally form 1 mg to 600 mg, and said pramipexole or pharmaceutically acceptable salt or solvate thereof, in an amount per unit form equivalent to from 0.125 mg to 21 mg, in particular from 0.125 mg to less than 1.6 mg, from 1.6 mg to 21 mg, from more than 4.5 mg to 21 mg or from more than 6 mg to 21 mg of pramipexole dihydrochloride monohydrate, are mixed together and formulated in a pharmaceutical composition, in admixture with a pharmaceutical carrier or vehicle, to be administered to the patient suffering from a depressive disorder, including MDD.

The Formulations

NK1-antagonist may be formulated in a pharmaceutical composition, wherein said NK1-antagonist is in admixture with a pharmaceutical carrier or vehicle. Pramipexole may also be formulated in a pharmaceutical composition, wherein said pramipexole is in admixture with a pharmaceutical carrier or vehicle.

In the above combinations, including fixed-dose combinations, of the present invention, the dose of pramipexole or pharmaceutically acceptable salt or solvate thereof, in pramipexole dihydrochloride monohydrate, per unit form, is from 0.125 mg to 45 mg, in an IR- or ER-formulation. Normally, i.e. in most patients suffering from a depressive disorder, including MDD, to be treated with said combination, said dose will range from 0.125 mg to 21 mg, in particular from 0.125 mg to less than 1.6 mg, advantageously from 1.6 mg 21 mg, from 1.8 mg to 21 mg, from 2.4 mg to 21 mg, to 3 mg to 21 mg, more advantageously from more than 4.5 mg to 21 mg, preferably from more than 6 mg to 21 mg from 10 mg to 21 mg, from 13 mg to 21 mg or from 15 mg to 21 mg.

It is hereby specified that pramipexole, or pharmaceutically acceptable salt or solvate thereof, at a dose per IR-unit form equivalent to from 0.125 mg to less than 1.6 mg, in particular from 0.125 mg to 1.5 mg of pramipexole dihydrochloride monohydrate dose per unit form, may possibly be used as titration doses at the beginning of the treatment of an adult patient or a pediatric patient, and that a dose per IR-unit form that is at least higher (1.08 times to 7 times higher) than the 1.5 mg maximum approved dose per IR unit form is needed to treat depression in adult patients. Thus, in order to be able to administer pramipexole at a daily dose of from more than 4.5 mg/day to 21 mg/day, advantageously from 5 mg/day to 21 mg/day, preferably from more than 6 mg/day to 21 mg day or from 15 mg to 21 mg, in combination with a NK1-antagonist, new IR-formulations are needed for treating a patient suffering from a depressive disorder, including MDD.

In particular, the dose of pramipexole or pharmaceutically acceptable salt or solvate thereof per IR-unit form, for the treatment of a depressive disorder, including MDD, will range from an amount equivalent to from 1.6 mg to 10.5 mg, from 1.8 to 10.5 mg, from 2.4 mg to 10.5 mg, from more than 3 mg to 10.5 mg, up to from 7.5 mg to 10.5 mg of pramipexole dihydrochloride monohydrate, depending on safety and tolerability (in combination with the NK1-antagonist).

The dose of pramipexole or pharmaceutically acceptable salt or solvate thereof per ER-unit form, for the treatment of a depressive disorder, including MDD, will range from an amount equivalent to from more than 4.5 mg to 21 mg, advantageously from more than 6 mg to 21 mg, up to from 15 mg to 21 mg of pramipexole dihydrochloride monohydrate, depending on safety and tolerability (in combination with the NK1-antagonist).

If the NK1-antagonist is aprepitant, the dose/unit form will range from 10 mg to 250 mg.

If the NK1-antagonist is rolapitant, the dose/unit form, in combination with pramipexole or pharmaceutically acceptable salt thereof at the above doses/unit form, will range from 30 mg to 270 mg.

The patients who tolerate pramipexole doses per unit form from more than 21 mg to 45 mg, or even higher, will have largely overcome the titration phase and will be regularly followed by their physician.

For their administration for the treatment of depressive disorder, including MDD, the NK1-antagonist and pramipexole or a pharmaceutically acceptable salt or solvate thereof are each formulated in a pharmaceutical composition in admixture with a pharmaceutical carrier or vehicle.

In the pharmaceutical compositions of the present invention for oral, subcutaneous, intravenous, transdermal or topical administration, the active ingredients are preferably administered in the form of dosage units, in admixture with the classic pharmaceutical carriers or vehicles, as set forth above.

The pharmaceutical compositions thus obtained are concurrently or sequentially administered to a patient suffering from a depressive disorder, including MDD.

Said NK1-antagonist and said pramipexole or a pharmaceutically acceptable salt or solvate thereof may also be formulated together in a fixed-dose combination consisting of a pharmaceutical composition comprising said pramipexole or a pharmaceutically acceptable salt or solvate thereof, and said NK1-antagonist, in admixture with a pharmaceutical carrier or vehicle.

The dosage, i.e. the amount of active ingredient in a single dose (amount per unit form) to be administered to the patient, can vary widely depending on the age, weight, and the health condition of the patient.

This dosage includes the administration of a NK1-antagonist dose from 1 μg to 600 mg, normally from 1 mg to 600 mg or from 1 mg to 300 mg, according to the potency of said NK1-antagonist and the age of the patient In general, the dose of pramipexole or pharmaceutically acceptable salt or solvate thereof is in an amount per IR-unit form, in pramipexole dihydrochloride monohydrate, of from 0.125 mg to 22.5 mg, from more than 1.5 mg to 22.5 mg, from 3 mg to 22.5 mg, from 5 mg to 22.5 mg, from 6.5 mg to 22.5 mg or from 7.5 mg to 22.5 mg, depending on safety and tolerability (in combination with the NK1-antagonist) and including doses per IR-unit form to be used in the titration period.

In general, the dose of pramipexole or pharmaceutically acceptable salt or solvate thereof, per ER-unit form, is an amount-range, in pramipexole dihydrochloride monohydrate, of from 0.125 mg to 45 mg, from more than 4.5 mg to 45 mg, from more than 6 mg to 45 mg, from 10 mg to 45 mg, from 13 mg to 45 mg or from 15 mg to 45 mg, depending on safety and tolerability (in combination with the NK1-antagonist).

Normally, the dose of pramipexole or pharmaceutically acceptable salt or solvate thereof per IR-unit form will be in an amount-range, in pramipexole dihydrochloride monohydrate, of from 0.125 mg to 10.5 mg, from 1.6 mg to 10.5 mg, from 3 mg to 10.5 mg, from 5 mg to 10.5 mg, from 6.5 mg to 10.5 mg or from 7.5 mg to 10.5 mg depending on safety and tolerability (in combination with the NK1-antagonist).

The dose per unit form of pramipexole or pharmaceutically acceptable salt or solvate thereof in an ER formulation, including slow-release compositions and transdermal therapeutic systems such as transdermal patches, will normally in a range that is equivalent to from 0.375 mg to 21 mg, from more than 4.5 mg to 21 mg, from more than 6 mg to 21 mg, from 10 mg to 21 mg, from 13 mg to 21 mg or from 15 g to 21 mg of pramipexole dihydrochloride monohydrate, depending on the tolerability (in combination with said NK1-antagonist).

As set forth above, the pramipexole doses/unit forms include low doses that can be used especially in the case of the titration of the pramipexole daily dose or in the less frequent case of use in the treatment of pediatric depressed patients.

The pharmaceutical compositions of the present invention are in unit form formulated with the classic excipients suitable for different ways of administration, as described above. Said unit forms are manufactured according to conventional technologies allowing, for example, the formulation of the NK1-antagonist in an IR-form and of pramipexole dihydrochloride monohydrate in ER-form in the same unit-form. Particularly advantageous are the formulations in the form of tablets, multi-score tablets, multi-layer tablets, coated tables, orally disintegrating tablets, extended release tablets, hard or soft capsules, multi-compartment capsules, extended-release capsules, patches for transdermal administration, liquid oral solutions, syrups or suspensions in a predetermined unit form, and vials for the intravenous or subcutaneous administration.

The pharmaceutical compositions may be formulated in oral unit forms such as tablets or gelatin capsules wherein pramipexole or a pharmaceutically acceptable salt or solvate thereof or the NK1-antagonist or both the active ingredients are in admixture with a carrier or vehicle that may include a diluent, such as cellulose, dextrose, lactose, mannitol, sorbitol or sucrose; a lubricant, such as, acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of pramipexole (or pharmaceutically acceptable salt or solvate thereof), or of NK1-antagonist, or of both the active ingredients. The oral formulations can also be in form of capsules allowing the extended release the pramipexole (or pharmaceutically acceptable salt or solvate thereof), or of NK1-antagonist, or of both the active ingredients.

As mentioned above, said oral unit forms may also be tablets or capsules wherein one of the active ingredient is in an IR-formulation and the other one is in an ER-formulation. For example said unit form comprises aprepitant or rolapitant in an IR-formulation and pramipexole dihydrochloride monohydrate in an ER-formulation, each at the amount per unit form as described above.

The pharmaceutical compositions may also be formulated in TTS, such as a patch formulation wherein the active ingredient or the mixture of the active ingredients may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

Accordingly, for example, pramipexole, preferably as a free base, may be formulated in a TTS, transdermally delivering a pramipexole effective dose, as described in "The pramipexole Component (b)" section, normally throughout the day; and, preferably, with a NK1-antagonist as described below, r, aprepitant be may formulated in an oral IR-form,
fosaprepitant meglumine may be formulated in a vial for injection, and
rolapitant may be formulated in an oral IR-unit form,
each at a dose per unit form as described in "The NK1-antagonist Component (a)" section.

In the case of pediatric or obese patients, the NK1-antagonist daily dose may be decided on the basis of the body weight. Thus, for example, aprepitant may be administered at a daily dose of from 0.67 to 2 mg/kg.

EXAMPLES

Example 1

A Phase I study was conducted in subjects receiving a single oral dose of pramipexole dihydrochloride monohydrate ("pramipexole") with or without a single oral dose of aprepitant. The study was a single center, single-blind study.

The objective of the study was to demonstrate that aprepitant could safely attenuate the gastro-intestinal side effects of pramipexole given in doses equivalent or higher than those approved in the treatment of Parkinson's Disease or shown in clinical trials to be effective in the treatment of depression.

To be enrolled in the study, participants the following inclusion/exclusion key criteria:

Key Inclusion Criteria
1. Male and female subjects aged 20-45 years old both ages included.
2. Females of childbearing potential must agree to be abstinent or else use any two of the following medically acceptable forms of contraception from the Screening Period through 14 days after the study Exit Visit: condom with spermicidal jelly, diaphragm or cervical cap with spermicidal jelly, or intrauterine device (IUD). A female whose male partner has had a vasectomy must agree to use one additional form of medically acceptable contraception. Subjects must agree to practice the above birth control methods for 14 days after the final visit as a safety precaution.
3. Females of non-childbearing potential, defined as surgically sterile (status post-hysterectomy, bilateral oophorectomy, or bilateral tubal ligation) or post-menopausal for at least 12 months, do not require contraception during the study. The reason must be documented in the source documents.

4. Males with female partners of childbearing potential must agree to use a highly effective, medically acceptable form of contraception from the Screening Period through 14 days after the study Exit Visit. Males with female partners of childbearing potential who themselves are surgically sterile (status post vasectomy) must agree to use condoms with spermicide over the same period of time. Male subjects must agree to practice the above birth control methods for 14 days after the final visit as a safety precaution.
5. Subjects must be in good health as determined by their medical history including personal and family psychiatric history and results of physical examination, electrocardiogram (ECG), vital signs, and laboratory tests. A subject with a medical abnormality may be included only if the investigator or designee considers that the abnormality will not introduce significant additional risk to the subject's health or interfere with study objectives.
6. Subjects must be able to clearly and reliably communicate changes in their medical condition.
7. Subjects with a body mass index (BMI) between 19.0 and 32.0 kg/m$^2$ (both inclusive).
8. Subjects able to swallow multiple pills or capsules simultaneously.
9. Subjects must have signed an informed consent form indicating that they understand the purpose of and procedures required for the study and are willing to participate in the study and comply with the study procedures and restrictions.

Key Exclusion Criteria:
The criteria for exclusion of a subject from enrollment in the study were as follows:
1. Any clinically relevant acute or chronic diseases which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of the study drugs.
3. History of substance abuse, known drug addiction, or positive test for drugs of abuse or alcohol.
4. History of drug or other significant allergy.
5. Known hypersensitivity to pramipexole, or to ondansetron or similar serotonin receptor antagonists, or to aprepitant or similar Substance P/NK1 receptor antagonists.
5. History of and/or current QT interval prolongation, congenital long QT syndrome, electrolyte abnormalities (e.g., hypokalemia or hypomagnesemia), congestive heart failure, bradyarrhythmias or other medicinal products that lead to QT prolongation or 1st degree AV block at Screening, Day −1, or pre-dose, ≥450 QTcF for males and ≥470 QTcF for females.
7. Treatment with centrally active drugs or antiemetics, within 1 months of study entry.
8. Tobacco or nicotine users (except subjects who stopped using tobacco or nicotine 1 year or more before enrollment in the study).
9. Excessive daily consumption of xanthines containing drinks (i.e. >500 mg/day of caffeine).
10. Subjects unwilling to curtail prolonged intensive physical exercise during the study conduct (from the Screening visit until the last dose of study drug).
11. Positive test result for hepatitis B surface antigen, hepatitis C antibody.
12. Positive test result for HIV 1 or 2 serology.
13. Likely to need any medical or dental treatment during the study period.
14. Use of any prescription or over-the-counter medication within 14 days prior to admission on Day −1. In addition any medications with central effects are prohibited for a period equal to 5 times the drug half-life prior to admission (Day −1), should this period be longer than 14 days.
15. Subjects unlikely to co-operate during the study, and/or be questionably compliant in the opinion of the investigator.
16. Subjects unable to be contacted in case of an emergency.
17. Intake of an investigational drug within 30 days of study entry.
18. Show evidence of suicidal ideation within the last 6 months as assessed by the C-SSRS (Columbia Suicide Severity Rating Scale) at Screening.

Following enrollment in the study, participants received single increasing oral doses of pramipexole given once daily in the morning (Period 1 of the study). The starting dose of pramipexole was 0.5 mg and the dose was increased daily by 0.5 mg increments. Once a subject had reached his/her first intolerable dose (FID-1), upward dose escalation was discontinued. First intolerable dose (FID) was defined as:
One (1) episode of vomiting; or
Two (2) episodes of retching, or
One (1) episode of severe nausea (Grade 3; defined as nausea interfering with activities of daily living or inadequate oral caloric or fluid intake; tube feeding, total parenteral nutrition or hospitalization indicated) lasting more than 1 hour, or
Three (3) consecutive episodes at every 4 hour ratings of moderate nausea (Grade 2; defined as subjectively symptomatic, but not interfering with activities of daily living), or
One (1) episode of moderate diarrhea (Grade 2; defined as 4-6 stools more than at baseline).

When a subject reached FID-1 on pramipexole alone, the subject was washed out for at least 5 days, and then entered Period 2 of the study during which the subject received single daily oral doses of pramipexole starting at 0.5 mg and titrated upward by 0.5 mg increments, together with oral aprepitant (80 mg) until subjects again reached an intolerable dose defined as above. The FID on oral pramipexole plus oral aprepitant was referred to as FID-2.

If a subject reached FID-2 during Period 2 at the same or lower dose than FID-1, and providing the investigator judged there were no safety issues and the subject was consenting, the subject received the same dose of pramipexole as the FID-2 dose together with a higher dose of oral aprepitant (120 mg) on the next day and the protocol specified that said subject should continue with the remainder of the dose titration with the higher dose of oral aprepitant (120 mg) until they reach the intolerable dose (FID2+). All other provisions of the protocol remained unchanged. Assessments were the same as those planned for the dose escalation day.

On each study day, subjects were followed up for up to 8 hours following drug administration for AEs, vital signs, ECGs. In addition, a laboratory panel was taken at screening and at the end of the study.

Four subjects were enrolled in the study. The following Table 1 summarizes the demographic characteristics of the subjects.

TABLE 1

Demographic Characteristics of Subjects Enrolled in the Study

| Subject ID | Gender | Age (years) | Baseline Weight (kg) |
|---|---|---|---|
| 1001 (019) | Female | 40 | 76.4 kg |
| 1006 (001) | Male | 41 | 99.1 kg |
| 1007 (004) | Male | 38 | 64.9 kg |
| 1008 (008) | Male | 39 | 81.8 kg |

All subjects reached FID-1 (pramipexole alone) during the study. The dose limiting toxicity was gastro-intestinal adverse events in all 4 subjects. During Period 2 of the study, all 4 subjects tolerated the maximum pramipexole dose allowed by the protocol of 6 mg and therefore none of them reached FID-2 (pramipexole with aprepitant). In other words, concomitant administration of aprepitant with pramipexole prevented the occurrence of dose-limiting gastro-intestinal adverse events associated with high doses of pramipexole. Table 2 lists for each subject the values for FID-1 (on pramipexole alone) and FID-2 (on pramipexole+aprepitant).

TABLE 2

Listing of First Intolerable Doses (FID) values

| Subject ID | FID-1 (Pramipexole alone) | FID-1 Dose Limiting Adverse Event | FID-2 Pramipexole + Aprepitant |
|---|---|---|---|
| 1001 | 2.5 mg | GI issues | >6.0 mg |
| 1006 | 0.5 mg | Moderate nausea | >6.0 mg |
| 1007 | 4.5 mg | Severe nausea | >6.0 mg |
| 1008 | 1.5 mg | Vomiting | >6.0 mg |

As shown in the following Table 3, the Maximum Tolerated Dose (MTD) during Period 2 was higher than MTD during Period 1 in all subjects, and in 3 subjects MTD-2 was increased by more than 3-fold.

TABLE 3

Listing of Maximum Tolerated Doses (MTD)

| Subject ID | MTD-1 (Pramipexole alone) | Maximal Tolerated Dose Pramipexole + Aprepitant | MTD2/MTD1 |
|---|---|---|---|
| 1001 | 2.0 mg | ≥6.0 mg | ≥3.0 |
| 1006 | NA (not tolerated at 0.5 mg) | ≥6.0 mg | ≥12.0 |
| 1007 | 4.0 mg | ≥6.0 mg | ≥1.5 |
| 1008 | 1.0 mg | ≥6.0 mg | ≥6.0 |

MTD: Maximum Tolerated Dose

Taken together, results showed that the co-administration of aprepitant with pramipexole attenuated dose-limiting gastro-intestinal adverse effects reported with pramipexole alone, thus showing that a NK1-antagonist enables the administration to a human being of pramipexole in doses otherwise non-tolerated when administering pramipexole alone.

In conclusion, the co-administration of aprepitant with pramipexole inhibited the occurrence of gastro-intestinal AEs associated with pramipexole given alone, thus enabling doses of pramipexole to be safely and tolerably raised by more than 2-fold, thereby allowing a far greater efficacy of this drug. In particular, these results show that the protective action of a NK1-antagonist allows the safe treatment of a human with pramipexole not only within the pramipexole approved dose range but also at doses that are higher than its maximum recommended dose, as well as at doses that are higher than a maximal tolerated dose of pramipexole when administered alone.

REFERENCES

Barone et al. 2010: Barone P, Poewe W, Albrecht S, Debieuvre C, Massey D, Rascol O, Tolosa E, Weintraub D. "*Pramipexole for the treatment of depressive symptoms in patients with Parkinson's disease: a randomised, double-blind, placebo-controlled trial.*" Lancet Neurol. 2010 June; 9(6):573-80. doi: 10.1016/S1474-4422(10)70106-X. Epub 2010 May 7.

Corrigan et al. 2000: Corrigan M H, Denahan A Q, Wright C E, Ragual R J, Evans D L; Corrigan M H, Denahan A Q, Wright C E, Ragual R J, Evans D; "*Comparison of pramipexole, fluoxetine, and placebo in patients with major depression*"; Depress Anxiety. 2000; 11(2):58-65.

Cusin et al. 2013: Cusin C, Iovieno N, Iosifescu D V, Nierenberg A A, Fava M, Rush A J, Perlis R H. *A randomized, double-blind, placebo-controlled trial of pramipexole augmentation in treatment-resistant major depressive disorder.* J Clin Psychiatry. 2013 July; 74 (7).

Dell'Osso et al 2013: Dell'Osso B, Ketter T A. *Assessing efficacy/effectiveness and safety/tolerability profiles of adjunctive pramipexole in bipolar depression: acute versus long-term data.* Int Clin Psychopharmacol. 2013 November; 28(6):297-304.

de Souza et al 2013: de Sousa R T, Zanetti M V, Brunoni A R, Machado-Vieira R. *Challenging Treatment-Resistant Major Depressive Disorder: A Roadmap for Improved Therapeutics.* Current Neuropharmacology, 2015, 13, 616-635.

Fawcett et al 2016: Fawcett J, Rush A J, Vukelich J, Diaz S H, DuNKllee L, Romo P, Yarns B C, Escalona R. *Clinical Experience With High-Dosage Pramipexole in Patients With Treatment-Resistant Depressive Episodes in Unipolar and Bipolar Depression.* Am J Psychiatry. 2016 Feb. 1; 173(2):107-11.

Goldberg et al 2004: Goldberg J F, Burdick K E, Endick C J. *Preliminary randomized, double-blind, placebo-controlled trial of pramipexole added to mood stabilizers for treatment-resistant bipolar depression.* Am J Psychiatry. 2004 March; 161(3):564-6.

Hori et al. 2012: Hori H, Kunugi H. *The efficacy of pramipexole, a dopamine receptor agonist, as an adjunctive treatment in treatment-resistant depression: an open-label trial.* Scientific World Journal. 2012; 2012:372474.

Kleeblatt et al 207: Kleeblatt J, Betzler F, Kilarski L L, Bschor T, Köhler S. *Efficacy of off-label augmentation in unipolar depression: A systematic review of the evidence.* Eur Neuropsychopharmacol. 2017 Mar. 16. pii: S0924-977X(17)30185-2.

Piercey 1998: Piercey M F. Pharmacology of pramipexole, a dopamine D3-preferring agonist, useful in treating Parkinson's disease. Clin Neuropharmacol 1998; 21:141-151.

Poon et al. 2013: Poon S, Sim K, Baldessarini R J. *Pharmacological Approaches for Treatment-resistant Bipolar Disorder.* Curr Neuropharmacol. 2015; 13(5): 592 604.

Schneider C S and Mierau J, 1987: Schneider C S, Mierau J *"Dopamine autoreceptor agonists: resolution and pharmacological activity of 2,6-diaminotetrahydrobenzothiazole and an aminothiazole analogue of apomorphine"*. J. Med Chem. 1987 March; 30(3):494-8.

Sienaert et al 2013: Sienaert P, Lambrichts L, Dols A, De Fruyt J. *Evidence-based treatment strategies for treatment-resistant bipolar depression: a systematic review*. Bipolar Disord. 2013 February; 15(1):61-9.

Tondo et al 2014: Tondo L, Vázquez G H, Baldessarini R J. *Options for pharmacological treatment of refractory bipolar depression*. Curr Psychiatry Rep. 2014 February; 16(2):431.

Willner et al. 1994: Willner P, Lappas S, Cheeta S, Muscat R. Reversal of stress induced anhedonia by the dopamine agonist, pramipexole. Psychopharmacol 1994; 115:454-462.

The invention claimed is:

1. A pharmaceutical combination comprising, as Component (a) a NK1-antagonist, in a pharmaceutical composition in dosage unit form comprising, as an active ingredient, said NK1-antagonist, in an amount per unit form of from 1 mg to 600 mg, in admixture with a pharmaceutical carrier or vehicle, and (b) pramipexole or a pharmaceutically acceptable salt or solvate thereof, in an amount per unit form equivalent to from 0.125 mg to 21 mg of pramipexole dihydrochloride monohydrate, in admixture with a pharmaceutical carrier.

2. The combination of claim 1, wherein said pramipexole or pharmaceutically acceptable salt or solvate thereof is in an amount per unit form equivalent to from more than 4.5 mg to 21 mg or from more than 6 mg to 21 mg of pramipexole dihydrochloride monohydrate.

3. The combination of claim 1, which is a fixed-dose combination consisting of a pharmaceutical composition comprising
   (a) said NK1-antagonist, in an amount per unit form of from 1 mg to 600 mg; and
   (b) pramipexole or a pharmaceutically acceptable salt or solvate thereof, in an amount per unit form equivalent to from 0.125 mg to 21 mg of pramipexole dihydrochloride monohydrate, in admixture with a pharmaceutical carrier or vehicle.

4. The combination of claim 3, wherein, in said pharmaceutical composition, said pramipexole or pharmaceutically acceptable salt or solvate thereof is in an amount per unit form equivalent to from more than 4.5 mg to 21 mg or from more than 6 mg to 21 mg of pramipexole dihydrochloride monohydrate.

5. The combination of claim 1, wherein said NK1-antagonist is aprepitant, in an amount per unit form in a range of from 10 mg to 250 mg.

6. The combination of claim 3, wherein said NK1-antagonist is aprepitant, in an amount per unit form in a range of from 10 mg to 250 mg.

\* \* \* \* \*